United States Patent [19]

Dasgupta et al.

[11] Patent Number: 5,660,992
[45] Date of Patent: Aug. 26, 1997

[54] SIALIC ACID/FUCOSE BASED ASSAY REAGENTS AND ASSAY METHODS

[75] Inventors: Falguni Dasgupta, Alameda; John Henry Musser, San Carlos, both of Calif.

[73] Assignee: Glycomed Incorporated, Alameda, Calif.

[21] Appl. No.: 464,507

[22] Filed: Jun. 5, 1995

Related U.S. Application Data

[62] Division of Ser. No. 78,949, Jun. 16, 1993, abandoned.

[51] Int. Cl.$^6$ .................. A61K 51/00; G01N 33/53; G01N 33/567; A61M 36/14
[52] U.S. Cl. .................. 435/7.1; 435/7.2; 435/7.21; 424/1.11
[58] Field of Search .................. 435/7.1, 7.2, 7.21; 424/1.11; 514/54

[56] References Cited

U.S. PATENT DOCUMENTS

| | | |
|---|---|---|
| 5,138,044 | 8/1992 | Dasgupta . |
| 5,143,712 | 9/1992 | Brandley et al. . |
| 5,198,424 | 3/1993 | McEver et al. . |
| 5,211,937 | 5/1993 | Brandley et al. . |
| 5,412,123 | 5/1995 | Rao et al. . |
| 5,426,178 | 6/1995 | Laine et al. . |
| 5,440,015 | 8/1995 | Macher et al. . |
| 5,484,891 | 1/1996 | Lasky et al. . |
| 5,489,578 | 2/1996 | Rosen et al. . |
| 5,498,604 | 3/1996 | Hasegawa et al. . |
| 5,519,008 | 5/1996 | Rao et al. . |
| 5,527,785 | 6/1996 | Bevilacqua et al. . |
| 5,541,287 | 7/1996 | Yau et al. . |
| 5,567,683 | 10/1996 | Nashed et al. . |

FOREIGN PATENT DOCUMENTS

| | | |
|---|---|---|
| WO9107993 | 6/1991 | WIPO . |
| WO9119501 | 12/1991 | WIPO . |
| WO9119502 | 12/1991 | WIPO . |
| WO9201718 | 2/1992 | WIPO . |
| WO9207572 | 5/1992 | WIPO . |
| WO9209293 | 6/1992 | WIPO . |
| WO9213887 | 8/1992 | WIPO . |
| WO9214757 | 9/1992 | WIPO . |
| WO9218610 | 10/1992 | WIPO . |
| WO9216612 | 10/1992 | WIPO . |
| WO9220708 | 11/1992 | WIPO . |
| WO9300908 | 1/1993 | WIPO . |
| WO9300919 | 1/1993 | WIPO . |

OTHER PUBLICATIONS

Allanson et al., "A Novel Mimic of the Sialyl Lewis x Determinant," (1993) Tetrahedron Letters 34(24):3945–3948.
Ball et al., *JACS*, vol. 114, No. 13, pp. 5449–5451 (1992).
Erbe et al., *J. Cell Biol.*, vol. 120, No. 5, pp. 1227–1235 (1993).
Gundel et al., "Endothelial Leukocyte Adhesion Molecule–1 Mediates Antigen–Induced Acute Airway Inflammation and Late–Phase Airway Obstruction in Monkeys," *J. Clin. Invest.*, 88:1407–1411 (10–1991).
Levy et al., "Cell Adhesion and Carbohydrates," *Annual Reports in Medicinal Chemistry*, 29:215–224 (1994).
Tyrell et al., *PNAS*, vol. 88, No. 22, pp. 10372–10376 (1991).
Mulligan et al., "Protective Effects of Oligosaccharides in P–Selectin–Dependent Lung Injury," *Nature*, 364:149–151 (1993).
Mulligan et al., "Role of Endothelial–Leukocyte Adhesion Molecule 1 (ELAM–1) in Neutrophil–Mediated Lung Injury in Rats," *J. Clin. Invest.*, 88:1396–1406 (1991).
Phillips et al., *Science*, vol. 258, pp. 1130–1132 (1990).
Geng et al., Journal of Biological Chemistry (1992) 267 (28):19846–19853.

(List continued on next page.)

*Primary Examiner*—Paula K. Hutzell
*Assistant Examiner*—N. M. Minnifield
*Attorney, Agent, or Firm*—Lyon & Lyon LLP

[57] ABSTRACT

Compounds that are synthetically inexpensive to make relative to the naturally occurring selectin ligands and that retain selectin binding activity are described that have a three-dimensionally stable configuration for sialic acid and fucose, or analogs or derivatives of these groups, such that sialic acid and fucose are separated by a non-carbohydrate linker that permits binding between those groups and the selectins, such compounds being represented by the following general structural formula I(a):

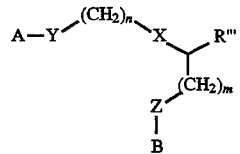

wherein m and n are independently an integer of from 1 to 5, Y and Z are independently a connecting moiety selected from the group consisting of —$CH_2$—, —O—, —S—, —NR' and —NR'R"— (wherein R' and R" are independently H or an alkyl containing 1 to 4 carbon atoms); X is a connecting moiety which is selected from the group consisting of —O—, —S—and —N—; and —R''' may be —R" or any moiety which does not interfere with the three-dimensional configuration of A or B so as to interfere with selectin binding and is preferably a moiety selected from the group consisting of —OR", —SR", —I, —$N_3$, and —NR'R" and A is selected from the group consisting of α and β forms of sialic acid, Kemp's acid, Quinic acid, Glyceric acid, Lactic acid and acetic acid, and esters thereof and B is selected from the group consisting of α and β forms of L-Fucose and esters and substituted forms thereof wherein one or more of the —OH groups is independently —F, or —$NR^{IV}$, $R^V$ wherein $R^{IV}$ and $R^V$ are independently an alkyl contain 1 to 5 carbons.

20 Claims, 6 Drawing Sheets

OTHER PUBLICATIONS

Geng et al., Journal of Biological Chemistry (1991) 266 (33):22313–22318.

Z. Szurmai et al., "Diethylene and Triethylene Glycol Spacers for the Preparation of Neoglycoproteins," Acta Chim, Hungarica, vol. 126, pp. 259–269 (1989).

T. Sugawara, "Synthesis of Omega–(Methoxycarbonyl) Alkyl and 9–(Methoxycarbonyl)–3,6–Dioxynonyl Glycopyranosides for the Preparation of Carbohydrate–Protein Conjugates," Carbohydr. Res., vol. 230, pp. 117–149 (1992).

F. Dasgupta et al., "Anti–Adhesive Therapeutics," Expert Opinion on Investigational Drugs, vol. 3, No. 7, pp. 709–724 (1994).

FIG. 1.
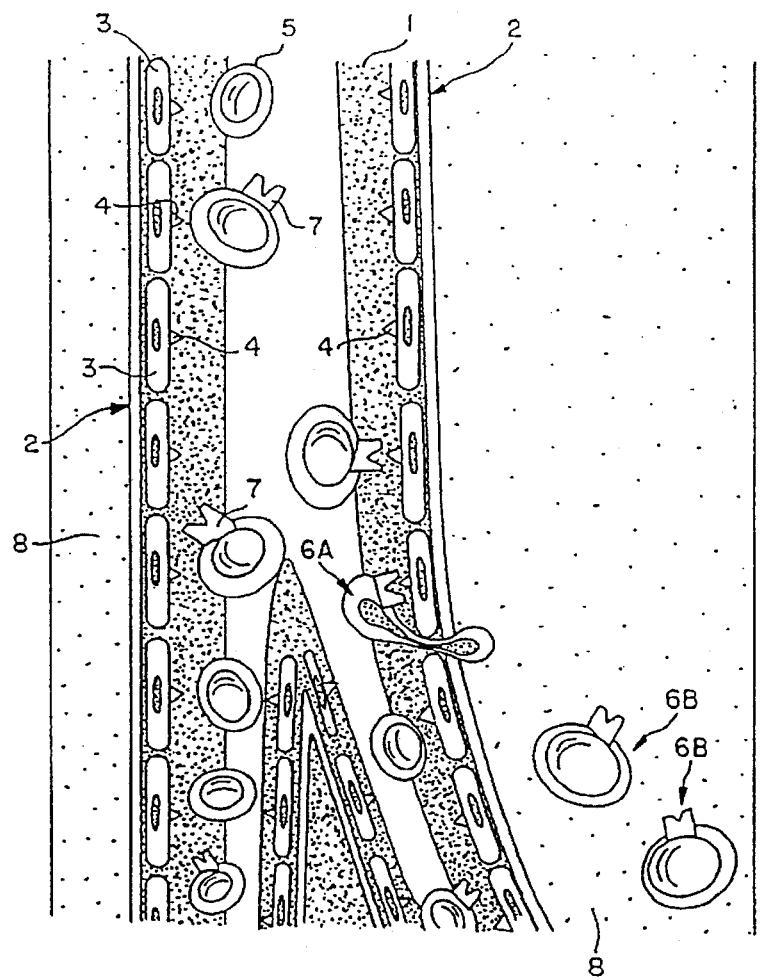
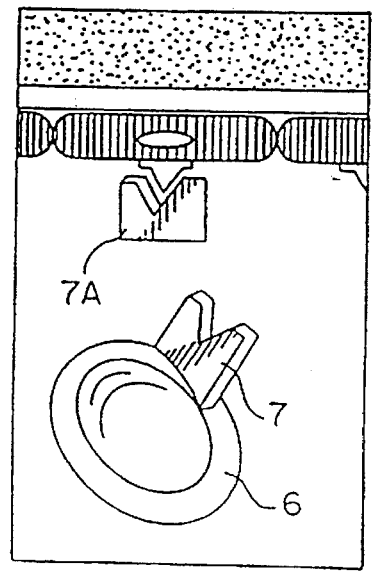
FIG. 2.

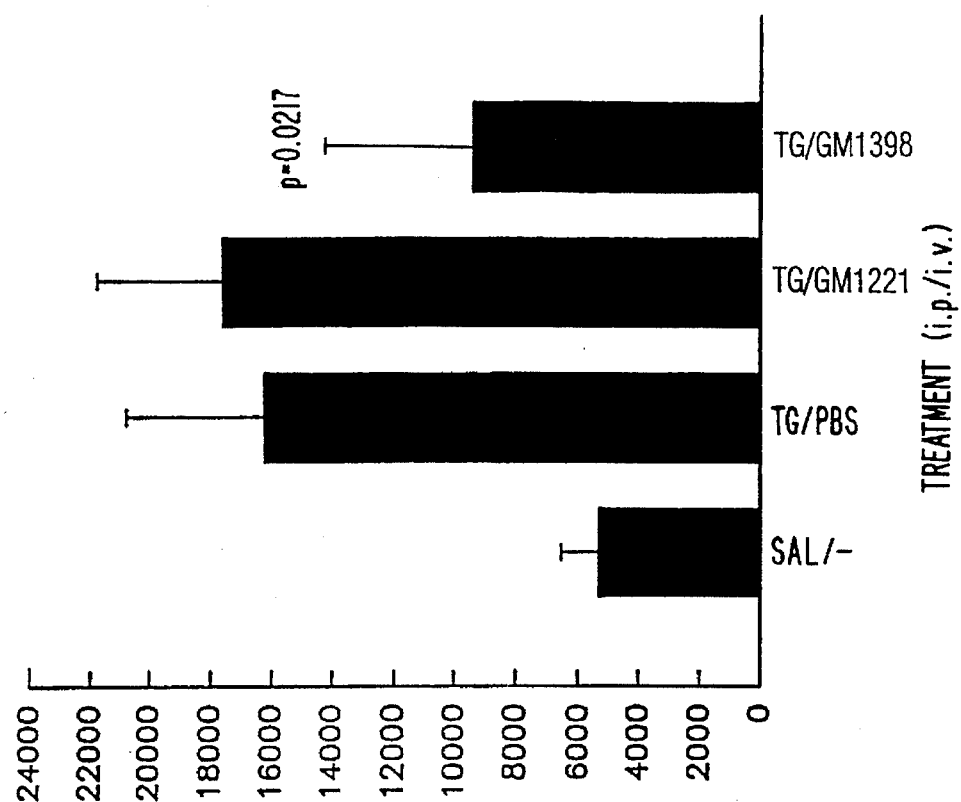
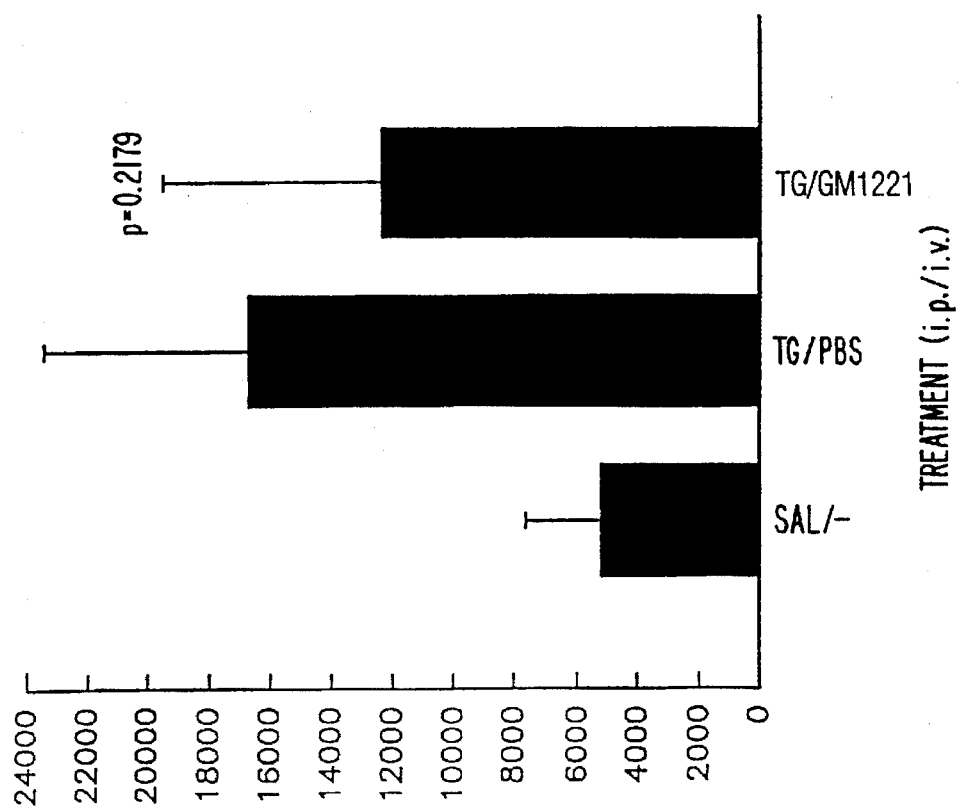

SIALIC ACID/FUCOSE BASED ASSAY REAGENTS AND ASSAY METHODS

This application is divisional of application Ser. No. 08/078949 filed Jun. 16, 1993, now abandoned.

FIELD OF THE INVENTION

This invention relates generally to the field of medicinal chemistry, and specifically to medicaments that are characterized by their capacity to bind to one or more of the three known selectins; LECAM-1, LECAM-2, or LECAM-3. The medicaments consist of three chemical moieties covalently linked in the following order: sialic acid, or an analogue or derivative thereof, a non-saccharide spacer, and fucose or an analogue or derivative thereof. Such medicaments have significant applications for diagnosis or prophylactic or therapeutic treatment of certain diseases including cancer, autoimmunity, and inflammation.

BACKGROUND OF THE INVENTION

A large body of data has been accumulated that establishes a family of receptors, the selectins (hereinafter LEC-CAMs) in certain diseases including cancer, autoimmunity, and in the inflammatory response. The three known members of this family, L-Selectin (LECAM-1, LAM-1, gp90MEL), E-Selectin (LECAM-2, ELAM-1) and P-Selectin (LECAM-3, GMP-140, PADGEM), each contain a domain with homology to the calcium-dependent lectins (C-lectins), an EGF-like domain, and several complement binding protein-like domains (Bevilacqua et al., *Science* (1989) 243:1160–1165; Johnston et al., *Cell* (1989) 56:1033–1044; Lasky et al., *Cell* (1989) 56:1045–1055; Tedder et al., *J. Exp. Med.* (1989) 170:123–133). It has been proposed that the selectins bind to particular ligands and that this accounts for their biological activity. Thus, drugs that interfere with or prevent binding of the ligands to the selectins will be useful medicaments for treating a variety of diseases.

For instance, adhesion of circulating neutrophils to stimulated vascular endothelium is a primary event of the inflammatory response, P-selectin has been shown to be centrally involved particularly as related to acute lung injury. Mulligan et al. have reported strong protective effects using anti-P-selectin antibody in a rodent lung injury model. (Mulligan, M. S. et al., *J. Clin. Invest.* (1991) 90:1600).

ELAM-1 is particularly interesting of the three selectins because of its transient expression on endothelial cells in response to IL-1 or TNF (Bevilacqua et al., *Science* (1989) 243:1160). The time course of this induced expression (2–8 h) suggests a role for this receptor in initial neutrophil extravasation in response to infection and injury. Indeed, Gundel et al. have shown that antibody to ELAM-1 blocks the influx of neutrophils in a primate model of asthma and thus is beneficial for preventing airway obstruction resulting from the inflammatory response. (Gundel R. H. et al,. *J. Clin. Invest.* (1991) 88:1407).

Several different groups have published papers regarding ELAM-1 ligands. Lowe et al., *Cell* (1990) 63:475 demonstrated a positive correlation between ELAM-1 dependent adhesion of HL-60 cell variants and transfected cell lines, with their expression of the sialyl Lewis x (sLex) oligosaccharide, Neu NAc α2-3Gal-β1-4(Fuc α1-3)-GlcNAc. By transfecting cells with plasmids containing an α(1,3/1,4) fucosyltransferase, they were able to convert non-myeloid COS or CHO lines into sLex-positive cells that bind in an ELAM-1 dependent manner. Walz et al., (1990) were able to inhibit the binding of a ELAM-1-lgG chimera to HL-60 cells with a monoclonal antibody directed against sLex or by glycoproteins with the sLex structure, but could not demonstrate inhibition with CD65 or CD15 antibodies. Both groups concluded that the sLex structure is the ligand for ELAM-1.

Information regarding the DNA sequences encoding endothelial cell-leukocyte adhesion molecules are disclosed in PCT published application WO90/13300 published Nov. 15, 1990 incorporated herein by reference. The PCT publication cites numerous articles which may be related to endothelial cell-leukocyte adhesion molecules. The PCT publication claims methods of identifying ELAM-ligands, as well as methods of inhibiting adhesion between leukocytes and endothelial cells using such ligands and specifically refers to MILAs which are described as molecules involved in leukocyte adhesion to endothelial cells.

As alluded to above, the ligand for ELAM, sLewis$^x$, consists of at least Sialic acid, fucose, and lactose. Lactose consists of galactose and glucose. Sialic acid and fucose are bound to the galactose and glucose moieties of lactose, respectively. Ligands that bind to the other selectins share similar structural features. Considering the obvious medical importance of selectin ligands, significant effort has been, and continues to be expended to identify the critical physical/chemical parameters associated with selectin ligands that enhance, or that are required for their activity. In no small part this effort is being driven by the need to have selectin ligands that are inexpensive to produce. It is generally thought that it will be commercially prohibitively expensive to produce naturally occurring sLewis$^x$ by either enzymatic or chemical synthesis because of the number of sophisticated reactions involved.

SUMMARY OF THE INVENTION

A first object of the invention is the description of medicaments that are selectin ligands that bind to certain selectins, and that are cost effective to synthesize.

A second object of the invention is the description of medicaments that are selectin ligands that bind to certain selectins wherein the ligands lack the lactose core structure of sLewis$^x$, and have substituted in its place a spacer moiety. Relative to sLewis$^x$, such medicaments are cost effective to synthesize.

A third object of the invention is a description of certain novel medicaments that incorporate newly discovered physical/chemical properties associated with sLewis$^x$ such that the medicaments have a three-dimensionally stable configuration for the presentation of the functional groups, sialic acid and fucose, of sLewis$^x$, that facilitates binding between those groups and receptors on the selectins. Such invention compounds are represented by the following general structural formula I:

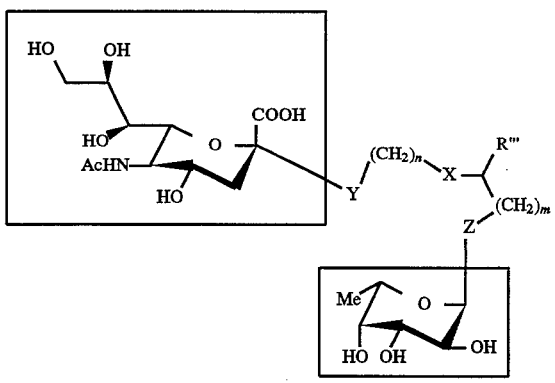

wherein m and n are independently an integer of from 1 to 5, Y and Z are independently a connecting moiety selected from the group consisting of —CH$_2$—, —O—, —S—, —NR' and —NR'R"— (wherein R' and R" are independently H or an alkyl containing 1 to 4 carbon atoms); X is a connecting moiety which is selected from the group consisting of —O—, —S—and —N—; and —R'" may be —R" or any moiety which does not interfere with the three-dimensional configuration of A or B so as to interfere with selectin binding and is preferably a moiety selected from the group consisting of —OR", —SR", —I, —N$_3$, and —NR'R", and A and B are the moieties having the saccharides shown in the boxes or analogues or derivatives thereof.

A fourth object of the invention is to provide a composition comprising selectin ligand medicaments bound to a detectable label and/or bound to a pharmaceutically active drug such as an anti-inflammatory drug.

A fifth object of the invention is to provide a pharmaceutical formulation containing selectin ligand medicaments which is useful in treating certain diseases.

A sixth object of the invention is to provide a description of methods to treat or diagnose disease.

A seventh object of the invention is to provide compositions and methods to determine the site of inflammation by administering labeled formulations of the type referred to above.

Another object of the invention is that the ligands can be labeled and the labeled ligands used in an assay to detect the presence of selectins in a sample.

These and other objects, advantages and features of the present invention will become apparent to those persons skilled in the art upon reading the details of the synthesis, structure, formulation and usage as more fully set forth below.

BRIEF DESCRIPTION OF THE DRAWINGS

This invention may be better understood and its numerous objects, advantages and features will become apparent to those skilled in the art by reference to the accompanying drawings as follows:

FIG. 1 is a cross-sectional schematic view showing the interaction between white blood cells and activated endothelial cells.

FIG. 2 is a cross-sectional schematic view showing how compounds of the invention would be used as pharmaceuticals to block ELAM-1.

FIG. 7 shows the effects of two compounds, GM 1221 and GM 1398 on thioglycollate induced peritonitis. Mice were injected with saline alone (sal/-), thioglycollate and phosphate buffered saline (TG/PBS) or thioglycollate and GM 1221 or GM 1398 (TG/GM 1221 or TG/1398), and the number of neutrophils in the peritoneal cavity measured.

DETAILED DESCRIPTION OF THE INVENTION

Figure 3:
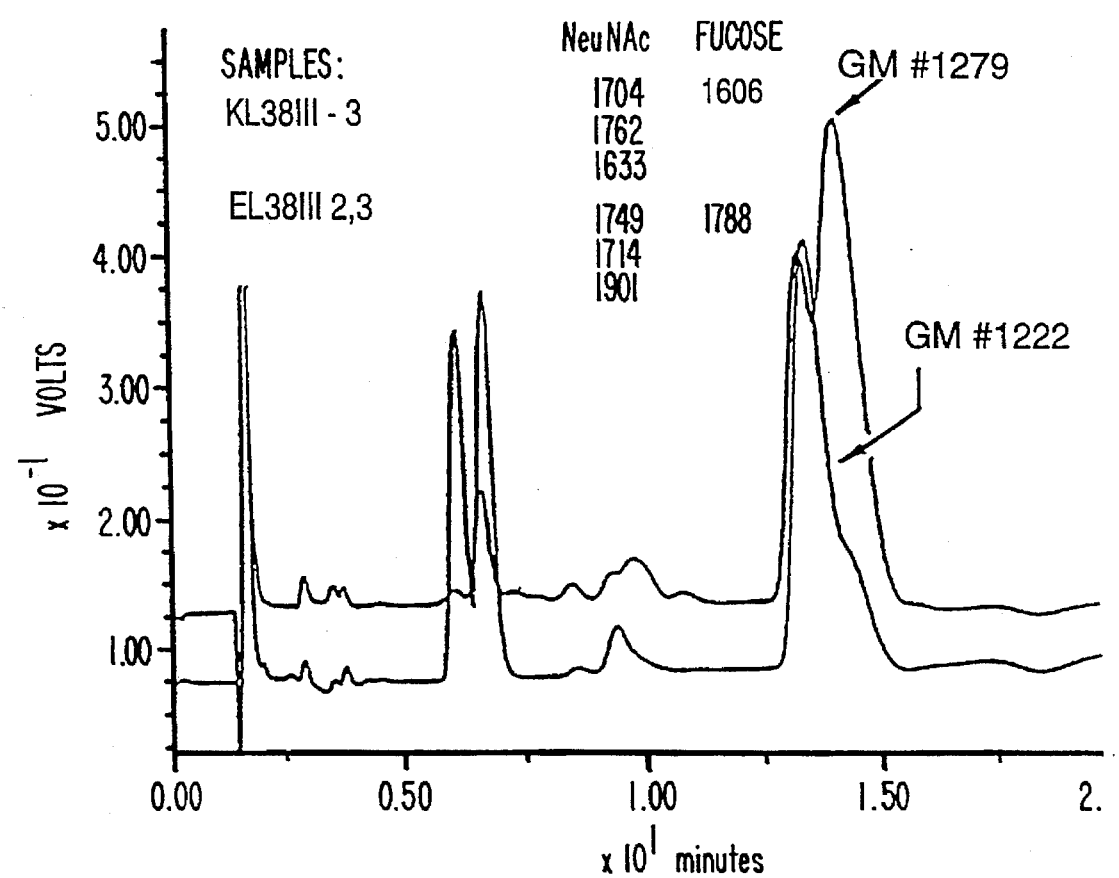
FIG. 3 is a graph showing the column chromatograph of two specific compounds; GM 1222 and GM 1279.

Throughout the description of the invention reference is made to certain publications including scientific articles and patents or patent applications. It is the intent that each of these publications be incorporated by reference when referred to in the specification.

Before the present invention compounds and compositions containing such and processes for isolating and using such are described, it is to be understood that this invention is not limited to the particular compositions, methods or processes described as such compositions and methods may, of course, vary. It is also to be understood that the terminology used herein is for the purpose of describing particular embodiments only, and is not intended to be limiting since the scope of the present invention will be limited only by the appended claims.

As used in this specification and the appended claims, the singular forms "a", "an" and "the" include plural referents unless the context clearly dictates otherwise. Thus, for example, reference to "an ELAM-1" includes reference to mixtures of such molecules, reference to "the formulation" or "the method" includes one or more formulations, methods and/or steps of the type described herein and/or which will become apparent to those persons skilled in the art upon reading this disclosure and so forth.

Some standard abbreviations used in connection with the present invention include: BSA, bovine serum albumin; DEAE, diethylaminoethyl; DMSO, dimethyl-sulfoxide; ELAM-1, endothelial/leukocyte adhesion molecule-1; HPTLC, high performance thin layer chromatography; LECAM-1, leukocyte/endothelial cell adhesion molecule-1; MOPS, 3-[N-Morpholino]propanesulfonic acid; NANA, N-acetylneuraminic acid; PVC, polyvinylchloride; TLC, thin layer chromatography; TFA, trifluoroacetic acid; Tris, tris (hydroxymethyl) aminomethane.

Development of the Invention

It is worth noting that while the invention compounds were selected for their capacity to bind to certain selectins, and that therefore this property is indicative of their medical activity, it cannot be excluded that they are also exerting their favorable medical effects, either in parallel or in tandem, through additional mechanisms of action. Thus, the skilled practitioner of this art will appreciate that a key aspect of the subject invention is the description of novel medicaments, and that Applicants intend not to be bound by a particular mechanism of action that may account for their prophylactic or therapeutic effects.

ELAM-1 has a lectin like domain that recognizes Sialyl Lewis (SLe$^x$)tetrasaccharide as shown below in structural formula II.

A key step in making the invention compounds was the realization that both SLe$^x$ and SLe$^a$ share a structural similarity in their three dimensional arrangements. Specifically, we observed that sialic acid and fucose, two functional epitopes in these tetrasaccharides, are juxtaposed in space in a way suitable for recognition by the selectins. Most importantly, for both tetrasaccharides we identified 4 to 12 atoms associated with the lactose core of the tetrasaccharides that functionally separate sialic acid from fucose. The 4 to 12 atoms excludes those defined as "Y" and "Z" in formula 1.

We postulated that replacement of these atoms would lead to compounds, such as those described and claimed herein, that maintain their selectin binding activity. While 4 to 12 is the preferred number of atoms, most preferred is 6 to 8 atoms as denoted, shown in the figure below by Roman numerals.

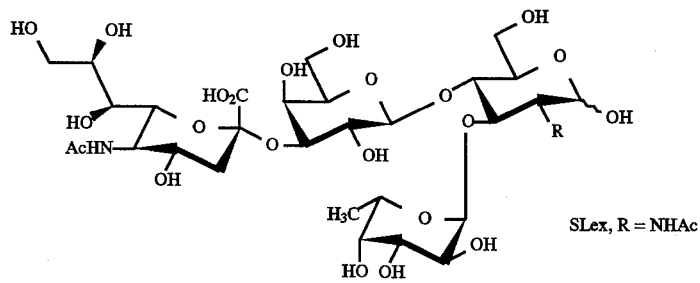

SLex, R = NHAc

The ability of SLe$^x$ to bind ELAM-1 is described by Lowe et al., *Cell* (1990) 63:475; Phillips et al., *Science* (1990) 250:1130; Walz et al., *Science* (1990) 250:1132; and Tyrrell et al., *Proc. Natl. Acad. Sci. USA* (1991) 88:10372.

It has also been shown (Berg et al., *J Biol Chem* (1991) 265:14869; Handa et al., *Biochem Biophys Res Commun* (1991) 181:1223) that both ELAM-1 and GMP-140 recognize the isomeric tetrasaccharide SLe$^a$ shown below as structural formula III.

For instance, a close structural examination of SLe$^x$ (shown in I) or a modification thereof wherein R=OH (SLe$^x$Glc) indicates that the epitopes i.e., α-Neu5Ac and L-Fucose, are linked through six atoms (Nos. 1–6) or eight atoms (Nos. i–viii) as shown in structural formula II(a) below.

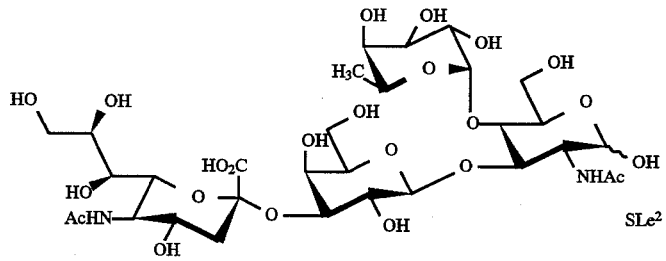

SLe$^a$

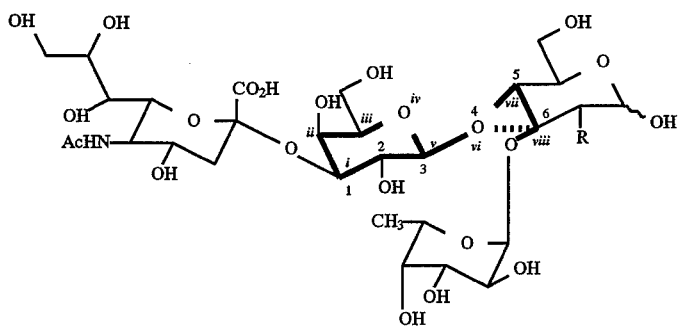

wherein R is —NHAc or —OH.

Based on this discovery, we deduced that the corresponding epitopes on the lectin domain of ELAM-1, and the other selectins, are spaced in a similar three-dimensional configuration such that maintenance of the 6 to 8 atoms in the ligand structure would yield active ligands that are markedly different in structure from the naturally occurring ligand.

Using these insights, we then designed certain selectin ligands. This may be done by attaching sialic acid and L-fucose as such, or analogs or derivatives thereof, through 4 to 12 atoms, or presently through six or eight atoms to provide a series of compounds shown as structural formula I. This series of compounds is designed to competitively inhibit selectins from binding to their natural ligands. These compounds can be combined with pharmaceutically acceptable excipients to provide pharmaceutical compositions useful in a wide range of treatments.

The structures that contain the appropriate reactive functions can be reacted with suitably protected hydrophobic carriers like ceramide or a ceramide mimic, steroids, diglycerides or phospholipids to form molecules that act as immunomodulators.

The compounds can act as antagonist ligand molecules, i.e. biochemical blocking agents by binding to selectins and preventing circulating neutrophils from binding to endothelial cells, thereby preventing a primary event involved in certain diseases, including the inflammatory response. Agonist ligands have the opposite effect.

The compounds of the present invention are designed to provide a three-dimensionally stable configuration for functional groups on sialic acid and fucose moieties so as to allow for binding between those groups and receptors on natural selectins. The compounds are represented by the following general structural formula I(a):

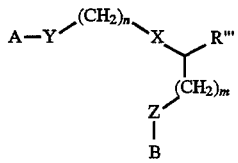

wherein m and n are independently an integer of from 1 to 5, Y and Z are independently a connecting moiety selected from the group consisting of —CH$_2$—, —O—, —S—, —NR' and —NR'R"— (wherein R' and R" are independently H or an alkyl containing 1 to 4 carbon atoms); X is a connecting moiety which is selected from the group consisting of —O—, —S— and —N—; and —R'" may be —R" or any moiety which does not interfere with the three-dimensional configuration of A or B so as to interfere with selectin binding and is preferably a moiety selected from the group consisting of —OR", —SR", —I, —N$_3$, and —NR'R", and A and B are as shown in structures IV and V respectively or analogues or derivatives thereof.

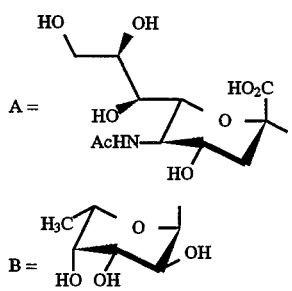

The compounds of general structural formula I(a) can be bound to known drugs, for example anti-inflammatory drugs so as to target the drug-selectin ligand complex to a particular site of disease. Additionally, they can be formulated to provide compositions useful in assaying a sample for the presence of selectins such as ELAM-1 and/or LECAM-1, or to detect the site of inflammation in a patient, or to treat acute inflammation (or treating the inflammatory symptoms of certain diseases) or other diseases involving the interaction of selectins on appropriate cell types.

In the general structural formula I(a) R'" has been generally defined to be any moiety which, when attached at the R'" position, will not interfere with the ability of the molecule as a whole to bind to a selectin receptor. More specifically, R'" will be an organic compound which contains hydrogen and carbon atoms alone or in combination with O, N and/or P. Specific examples of R'" include:

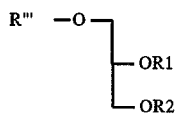

wherein R1 and R2 are independently an alkyl, or alkenyl, preferably an alkyl containing 1–5 carbons or containing 13 to 15 carbons;

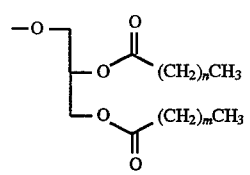

wherein n and m are each independently an integer of from 15 to 24 and wherein the alkyl group may be saturated or unsaturated;

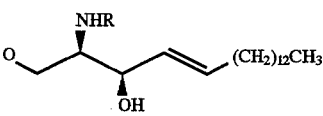

wherein R is —CO(CH$_2$)$_{14}$CH$_3$;

```
CH2—O—(CH2)17CH3
|
O—CH
|        O
|        ||        +
CH2—P—(CH2)2N(CH3)3;
|
O—
```

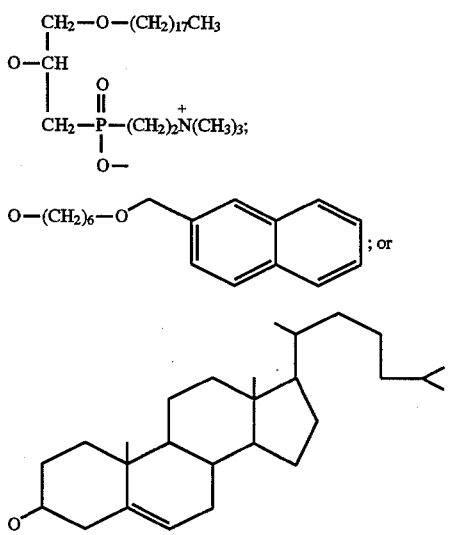

The preferred example of A and B are shown, respectively, in formula IV and V. Other examples of A include α- or β- or other analogues or derivatives of sialic acid other than the N-acetyl neuraminicacid residue shown in formula IV, Kemp's acid, glyceric acid, lactic acid, acetic acid and —SO$_3$ and —PO$_3$. The synthesis of certain analogues of sialic acid is described in U.S. Pat. No. 5,138,044.

Preferred forms of B are the α and β forms of L-Fucose as shown in formula V. The moiety B also includes substituted forms of the following fucose structure V(a):

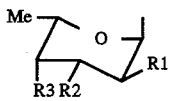

wherein Me is a methyl group, R1, R2 and R3 are each independently —OH, —F, —NR"R'" (wherein R" and R'" are independently alkyls containing 1 to 5 carbon atoms). Other moieties for B include modified fucosides such as corresponding carboxylic analogues of fucose; inositol; substituted inositol; benzimidazole; substituted benzimidazole; guanidine; substituted butane, wherein substituents include —CH$_2$, —CHR1, —CHR2, CH$^2$R3 and R1, R2, and R3 are independently OH, F or NR"R'"; pentaerythritol and substituted pentaerythritol.

Assaying Compounds of Formula I(a)

The compounds of formula I(a) can be tested for their ability to bind to a selectin receptor and/or block the binding site of the receptor and thereby prevent a natural ligand from binding to the selectin receptor, A generalized procedure for testing the compounds of formula I(a) is given below.

An ELISA assay is preferably used that employs recombinant fusion proteins composed of extracellular portions of the human selectins joined to human immunoglobulin heavy chain CH3, CH2, and hinge regions. See, for example, Walz et al., Science (1990) 250:1132; Aruffo et al., Cell (1991) 67:35; Aruffo et al., Proc. Natl. Acad. Sci. USA. (1992) 89:2292. The assay is well known in the art, and generally consists of the following three steps:

I. 2,3sLex glycolipid (25 picomole/well) is transferred into microtiter wells as solutions and then evaporated off. Excess, which remained unattached is washed off with water. The wells are then blocked with 5% BSA at room temperature for an hour and then washed with PBS containing 1 mM calcium.

II. Preparation of "multivalent" receptor of the Selectin-IgG chimera is carried out by combining the respective chimera (1 ug/mL) with biotin labelled goat F(ab')$_2$ anti-human IgG (Fc specific) and streptavidinalkaline phosphatase diluted 1:1000 in 1% BSA-PBS (1 mM calcium) and incubating at 37° C. for 15 min. This allows the soluble multivalent receptor complex to form.

III. Potential inhibitors such as compound of formula I(a) are allowed to react with the soluble receptor at 37° C. for 45 min. This test assumes that optimal binding, between the soluble phase receptor complex and the inhibitor (non natural ligand), occurs within this time frame. This solution is then placed in the microtiter wells that were prepared in step I. The plate was incubated at 37° C. for 45 minutes to allow the soluable receptor to bind to its natural ligand. In the presence of a strong only a few receptors should be free to bind to the microtiter plate coated with the natural ligand.

The positive control is the signal produced by the soluble receptor when it is allowed to react with 2,3sLex glycolipid in the microtiter wells in the absence of any inhibitor. This is considered 100% binding. The signal produced by the receptor that has been previously treated with an inhibitor (recorded as O.D.), is divided by the signal produced by the positive control and multiplied by 100 to calculate the % receptor bound to the well in the presence of the inhibitor. The reciprocal of this is the % inhibition.

Referring now to FIG. 1, a cross-sectional view of a blood vessel 1 is shown. The vessel wall 2 is lined internally with endothelial cells 3. The endothelial cells 3 can be activated causing the cells 3 to synthesize ELAM-1 which is displayed in FIG. 1 as a triangular surface receptor 4. Both red blood cells 5 and white blood cells (6A, 6B) flow in the vessel 1. The white blood cells display carbohydrate ligands 7 which have chemical and physical characteristics which allow the ligands 7 to bind to the receptors 4. Once the ligand 7 binds to the receptor 4, the white blood cell is brought through the vessel wall 2 as is shown with the white blood cell 6A. The white blood cells 6B brought into the surrounding tissue 8 can have positive effects, such as fighting infection, and negative effects, such as inflammation.

An important aspect of the present invention can be described by referring to FIG. 2. The compounds of a formula I(a) are shown as 7A and can adhere to a selectin such as ELAM-1 by themselves and can be formulated into pharmaceutical compositions, which when administered will effectively block the ELAM-1 and prevent the adhesion of a ligand 7 connected to a white blood cell 6. By administering pharmaceutically effective amounts of the compounds 7A, some, but not all, of the white blood cells will not reach the surrounding tissue. By slowing the rate at which the white blood cells reach the surrounding tissue, inflammation can be prevented and/or alleviated.

It is known that for an acute inflammatory response to occur, circulating neutrophils must bind to and penetrate the vascular wall and access the site of injury. Several molecules have been implicated in this interaction, including a family of putative carbohydrate ligands and their receptors. One molecule that was previously identified is the endogenous carbohydrate ligand for endothelial leukocyte adhesion molecule-1 (hereinafter ELAM-1). The present invention provides a family of molecules which bind as the endogenous ligands and thereby block other selectin receptors such as LECAM-1 receptors.

The compounds of Formula I(a) may also be labeled using standard radioactive, fluorescent, enzymic or other label for analytical or diagnostic purposes. In general, the significant portion of the compounds of Formula I(a) is the compound shown; the embodiments of the substituent R'" will depend on the intended use. Suitable embodiments for this substituent will be apparent to those of skill in the art.

Preferred embodiments of the ligands of the invention are those wherein the substituent represented by A or B is an N-acetylneuramyl residue and B is fucose.

In order for a ligand of the invention to bind to a selectin receptor such as an ELAM-1 receptor the ligand need not include the identical atoms in the identical configuration as per structural formula I(a) but must have (1) a stable three dimensional conformation as shown in formula I(a) or (2) a substantially equivalent configuration to that shown in formula I(a). The equivalency of any other ligand will relate to its physical three dimension structure and the electron configuration of the molecule and in particular the charge related characteristics presented by the groups present on the A and B moieties shown in formulae IV and V. In order for a molecule of the invention to have a substantially equivalent structure to that shown in formula I(a) the molecule must bind to a selectin receptor (e.g. an ELAM-1 receptor) to the same degree or greater as the compound of formula I(a) when the molecule is allowed to bind to the receptor under physiological conditions.

Assay to Identify Ligand (General)

Candidate ligands can be assayed for their ability to adhere to ELAM-1. The method comprises attaching candidate ligands of formula I(a) to a substrate surface and then contacting the substrate surface thereon with recombinant cells, that are genetically engineered to express high levels of ELAM-1, for a sufficient time to allow the cells to adhere to the substrate bearing the candidate ligand. Thereafter, centrifugal force or other appropriate methodology is applied so as to separate away the cells which do not adhere to the substrate. Candidate ligands which adhere to ELAM-1 are determined via the labels on the cells. Such molecules are isolated, characterized, and their structure specifically identified.

Radiolabeled COS cells expressing cell surface ELAM-1 can be used as probes to screen compounds of the invention. ELAM-1 transfected COS cells will adhere to a subset of compounds of the invention which can be resolved on TLC plates Or adsorbed on PVC microtiter wells. Adhesion tests are preferably done under physiological conditions. Adhesion to these compounds may require calcium, but will not be inhibited by heparin, chondroitin sulfate, keratin sulfate, or yeast phosphomannan (PPME). Monosaccharide composition, linkage analysis, and FAB mass spectrometry of the purified compounds will indicate that the ligands for ELAM-1 share common structural characteristics which generally relate to the moieties A and B and the position in which they are held.

One mechanism by which the compounds of the invention could mediate intercellular events would involve the recognition of these compounds on one cell (e.g., an endothelial cell) by a specific carbohydrate-binding protein (lectin) on an opposing cell (e.g., a leukocyte). Data generated in connection with the present invention indicate that acidic glycolipids isolated from leukocytes and ELAM-1 function as such an oligosaccharide-lectin pair, participating in the interaction of neutrophils with the surface of cells of activated vascular endothelium. Many protein-protein interactions have been implicated in neutrophil-endothelium transmigration (see Lo et al., *J. Immunol.* (1989) 143:3325; Osborn et al., *Cell* (1989) 59:1203; Larsen et al., *Cell* (1989) 59:305; and Arnaout *Blood* (1990) 75:1037). The present inventors believe it is likely that this lectin-carbohydrate interaction is only one step in a series that result in neutrophil extravasation. The adhesion of ELAM-1 for compounds of the invention has been tested. Accordingly, such compounds are believed to be useful in mediating a specific, but possibly weak adhesion that is then stabilized and elaborated by the participation of other receptors. Compounds with the structural and functional characteristics described herein, or modifications of these structures, are believed to be capable of blocking the interaction of neutrophils with activated vascular endothelium mediated by ELAM-1, and hence provide useful pharmaceutically active agents which can interrupt the adverse effects involved in the interaction of ELAM-1 and circulating neutrophils, e.g., prevent or reduce inflammation.

Identification of Compounds Which Act as ELAM-1 Ligands Using Recombinantly Produced Receptor A complete cDNA for the ELAM-1 receptor was obtained by PCR starting with total RNA isolated from IL-1 stimulated human umbilical vein endothelium. The resulting cDNA was inserted into the CDM8 plasmid (see Aruffo et al., *Proc Natl Acad Sci USA* (1987) 84:8573) and the plasmid amplified in *E. coli* Plasmid DNA from individual colonies was isolated and used to transfect COS cells. Positive plasmids were selected by their ability to generate COS cells that support HL-60 cell adhesion. DNA sequencing positively identified one of these clones as encoding for ELAM-1 (Bevilacqua et al., *Science*, (1989) 243:1160; Polte et al., *Nucleic Acids Res* (1990)18:1083; Hession et al., *Proc Natl Acad Sci USA* (1990) 87:1673). These publications are incorporated herein by reference for their disclosure of ELAM-1 and genetic material coding for its production. The complete nucleotide sequence of the ELAM-1 cDNA and predicted amino acid sequence of the ELAM-1 protein are given in the above cited article by Bevilacqua et al., which DNA and amino acid sequences are incorporated herein by reference (see also published PCT U.S. patent application WO90/13300 which was published Nov. 15, 1990, which is incorporated herein by reference).

COS cells, expressing membrane-bound ELAM-1, were metabolically radiolabeled with $^{32}PO_4$. These labeled cells can be used as probes in two assay systems to screen for recognition of the compounds of formula I(a). More specifically, compounds of formula I(a) may be adsorbed to the bottoms of PVC microtiter wells or resolved on TLC plates. In either assay the compounds may be probed for their ability to support adhesion of ELAM-transfected COS cells, untransfected COS cells, or COS cells transfected with a plasmid containing an irrelevant cDNA, under conditions of controlled detachment force (see Swank-Hill et al., *Anal Biochem* (1987) 183:27; and Blackburn et al., *J. Biol Chem.* (1986) 261:2873 each of which is incorporated herein by reference to disclose the details of such assaying methodology).

It has been indicated that R'" of structural formula 1(*a*) may be a linker which may be any suitable and attachable moiety including a ceramide or a protein or peptide and is preferably a group with a reactive group thereon which allows it to covalently bind to a substrate or pharmaceutically active drug. In one embodiment of the invention the "linker" connects one or more ligands to a support base. The support base is then contacted with a sample to assay for the presence of a desired selectin in the sample.

The "linker" can be used to attach a pharmaceutically effective drug to the compound at the R' position. The (Ligand-Linker-Drug) conjugate thus formed provides an effective drug delivery system for the linked drug: A method of attaching any moiety at the R' position is shown in Reaction Scheme V.

NSAID or non-steroidal, anti-inflammatory drugs such as naproxen or ibuprofen which act as anti-inflammatory agents could be administered bound to the modified ligand and could be administered systemically in smaller amounts than usual while obtaining an equivalent effect or even greater anti-inflammatory effect at the site of inflammation. Any other drugs which might be attached include, but are not limited to, antibiotics, vasodilators and analgesics. Such a drug delivery system would reduce any systemic effect normally caused by the drug in that the drugs could be administered in amounts of one-half to one-tenth the normal dose and still obtain the same anti-inflammatory result at the site of inflammation.

Method of Synthesis (General)

The compound of formula I(a) can be made using the general and specific synthesis schemes and examples described below. However, those skilled in the art will recognize variations thereof which are intended to be encompassed by the present invention. In general, the A and B moieties of formula I(a) must be connected and held in a desired three-dimensional configuration. A simple reaction scheme for accomplishing such is shown below:

SCHEME I

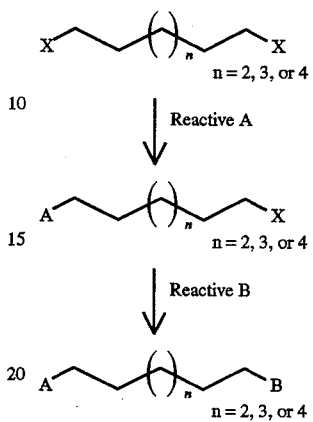

wherein each X is independently selected from the group consisting of —OH, —NH$_2$, —SH, and halogens such as Cl and Br; A and B are, respectively, a sialic acid and L-Fucose and their respective bioisosteres. A more specific version of reaction Scheme I is shown below:

REACTION SCHEME II

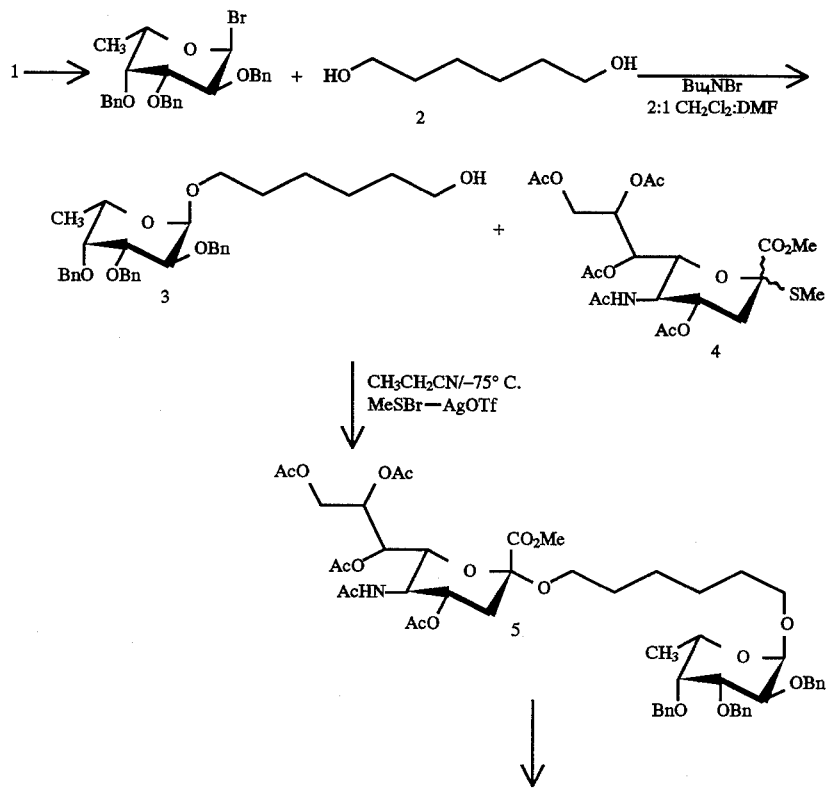

-continued
REACTION SCHEME II
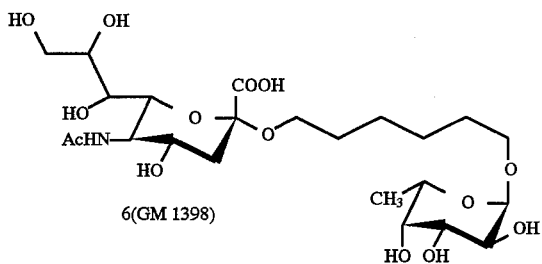
6(GM 1398)
A reaction scheme wherein the fucose is attached is shown below.
REACTION SCHEME III
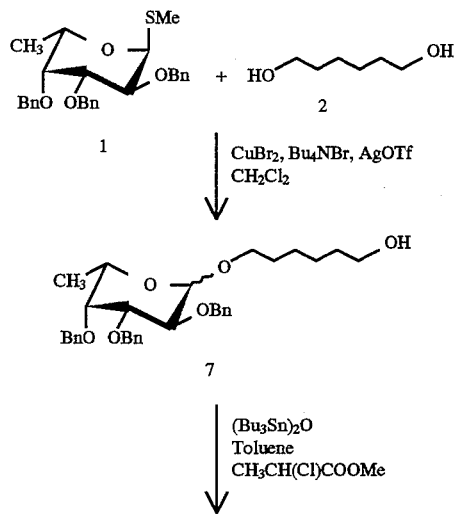
-continued
REACTION SCHEME III
Another version of a reaction scheme wherein A and B are in the desired configuration is given below:
REACTION SCHEME IV
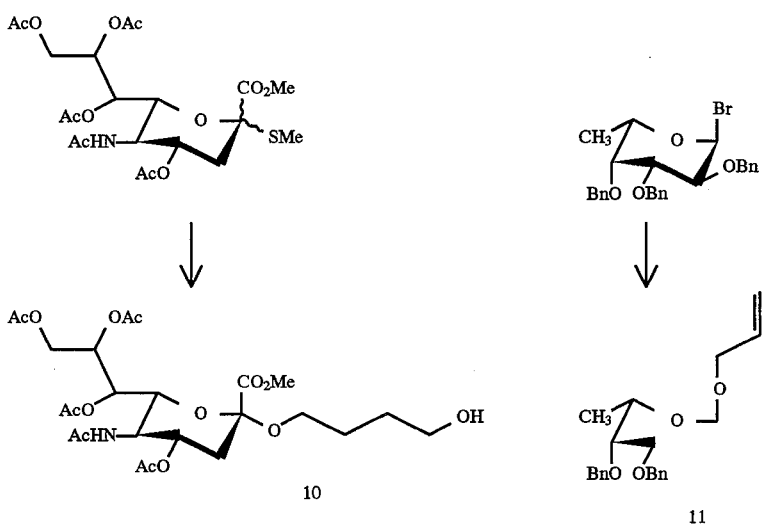

-continued
REACTION SCHEME IV
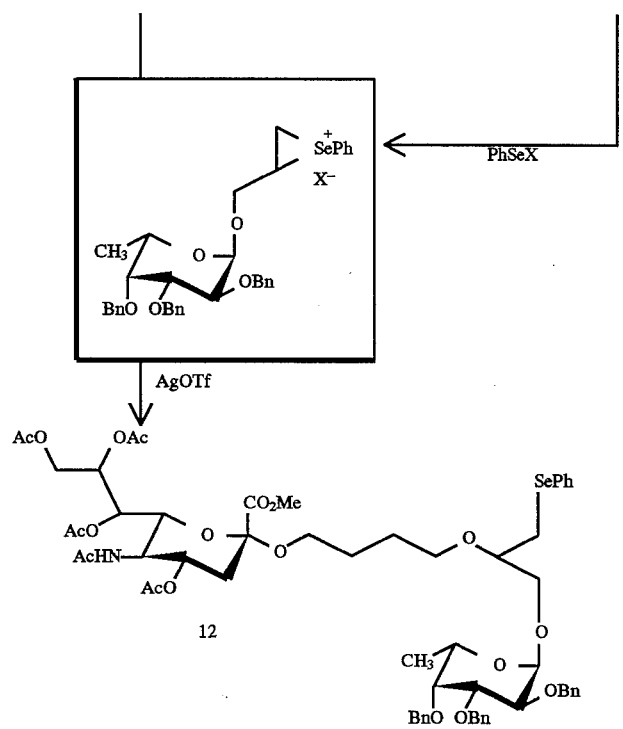
It is possible to alter a compound of formula I(a) to obtain a compound which is labeled or attached to any other desired compound.
A general reaction scheme for obtaining such is as follows:
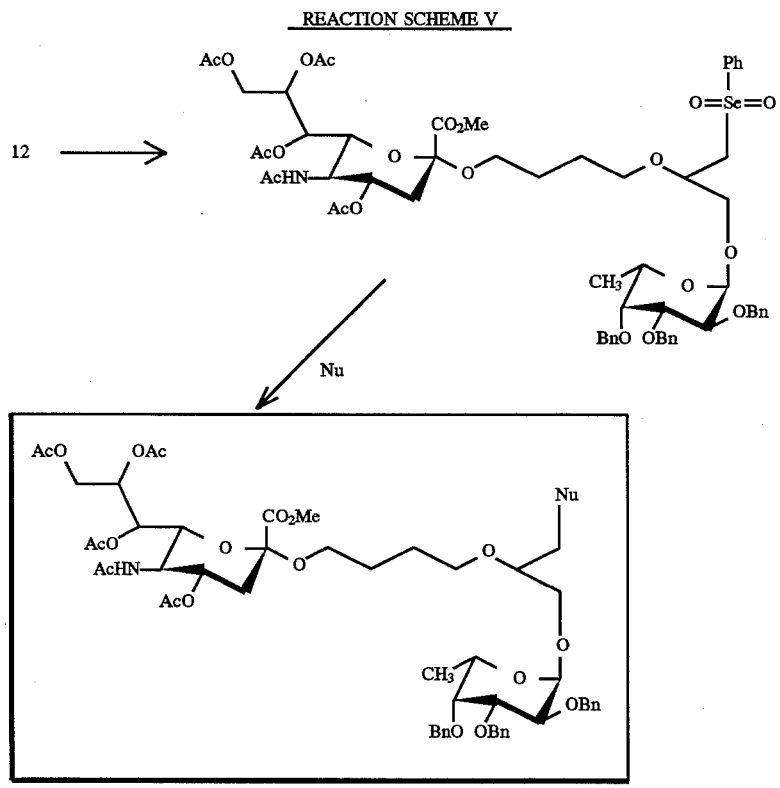

The compound shown above can then be reacted with a fluorescent probe, a multivalent compound, a ceramide, cholesterol or other lipid components, or a pharmaceutically active drug such as an anti-inflammatory drug.

Use and Administration

The compounds of the invention such as various ligands of structural Formula I(a) can be administered to a subject in need thereof to treat the subject by either prophylactically preventing inflammation or relieving it after it has begun. The ligands are preferably administered with a pharmaceutically acceptable carrier, the nature of the carrier differing with the mode of administration, for example, oral administration, usually using a solid carrier and I.V. administration a liquid salt solution carrier. The formulation of choice can be accomplished using a variety of excipients including, for example, pharmaceutical grades of mannitol, lactose, starch, magnesium stearate, sodium saccharin cellulose, magnesium carbonate, and the like. Oral compositions may be taken in the form of solutions, suspensions, tablets, pills, capsules, sustained release formulations, or powders. Particularly useful is the administration of the compounds directly in transdermal formulations with permeation enhancers such as DMSO. Other topical formulations can be administered to treat dermal inflammation.

A sufficient amount of compounds would be administered to bind to a substantial portion of the selectin expected to cause or actually causing the disease, for example, inflammation so that inflammation can either be prevented or ameliorated. Thus, "treating" as used herein shall mean preventing or ameliorating the appropriate disease. Typically, the compositions of the instant invention will contain from less than 1% to about 95% of the active ingredient, preferably about 10% to about 50%. Preferably, between about 10 mg and 50 mg will be administered to a child and between about 50 mg and 1000 mg will be administered to an adult. The frequency of administration will be determined by the care given based on patient responsiveness. Other effective dosages can be readily determined by one of ordinary skill in the art through routine trials establishing dose response curves.

When determining the dose of compounds to be administered which block selectin receptors, it must be kept in mind that one may not wish to completely block all of the receptors. In order for a normal healing process to proceed, at least some of the white blood cells or neutrophils must be brought into the tissue in the areas where the wound, infection or disease state is occurring. The amount of the ligands administered as blocking agents must be adjusted carefully based on the particular needs of the patient while taking into consideration a variety of factors such as the type of disease that is being treated.

It is believed that the compounds of the present invention can be used to treat a wide range of diseases, including diseases such as rheumatoid arthritis and multiple sclerosis. The compositions of the invention should be applicable to treat any disease state wherein the immune system turns against the body causing the white cells to accumulate in the tissues to the extent that they cause tissue damage, swelling, inflammation and/or pain. The inflammation of rheumatoid arthritis, for example, is created when large numbers of white blood cells quickly enter the joints in the area of disease and attack the surrounding tissues.

Formulations of the present invention might also be administered prevent the undesirable aftereffects of tissue damage resulting from heart attacks. When a heart attack occurs and the patient has been revived, such as by the application of anticoagulants or thrombolytic (e.g., tPA), the endothelial lining where a clot was formed has often suffered damage. When the antithrombotic has removed the clot, the damaged tissue beneath the clot and other damaged tissue in the endothelial lining which has been deprived of oxygen become activated. The activated endothelial cells then synthesize the ELAM-1 receptors within hours of the cells being damaged. The receptors are extended into the blood vessels where they adhere to glycolipid ligand molecules on the surface of white blood cells. Large numbers of white blood cells are quickly captured and brought into the tissue surrounding the area of activated endothelial cells, resulting in inflammation, swelling and necrosis which thereby decreases the likelihood of survival of the patient.

In addition to treating patients suffering from the trauma resulting from heart attack, patients suffering from actual physical trauma could be treated with formulations of the invention in order to relieve the amount of inflammation and swelling which normally result after an area of the body is subjected to severe trauma. Other disease states which might be treatable using formulations of the invention include various types of arthritis and adult respiratory distress syndrome. After reading the present disclosure, those skilled in the art will recognize other disease states and/or symptoms which might be treated and/or mitigated by the administration of formulations of the present invention.

Other modes of administration will also find use with the subject invention. For instance, the ligand molecules of the invention can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), preferably about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

The compounds of the instant invention may also be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles. Compounds of Formula I can be mixed with compatible, pharmaceutically acceptable excipients.

Suitable vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g. Remington's Pharmaceutical Sciences, Mack Publishing Company, Easton, Pa., 17th edition, 1985. The composition or formulation to be administered will, in any event, contain a quantity of the compounds adequate to achieve the desired state in the subject being treated.

The various compounds of the present invention can be used by themselves or in combination with pharmaceutically acceptable excipient materials as described above. However, the compounds Of the invention can be made as conjugates wherein they are linked in some manner (e.g., via the R' moiety) to a label. By forming such conjugates, the compounds can act as biochemical delivery systems for the label so that a site of disease can be detected.

For instance, carbohydrates can be labelled by a variety of procedures, for example: esterification of hydroxyl bonds to form a structure capable of complexing directly with a radioisotope or nmr enhancer; reaction of the carbohydrate with amino diacetic acid (IDA) in organic solvent-to form an N-linked glycoside derivative which would be capable of complexing with a radioisotope via the nitrogen and oxygen atoms of the IDA group; or coupling of the carbohydrate to amino acids which may be labelled directly (e.g. cysteine, tyrosine) or labelled via a bifunctional chelating agent (e.g., lysine).

Appropriate radioactive atoms would include, for example, technetium 99 m ($^9$mm Tc), iodine-123 ($^{123}$I) or indium-111 ($^{111}$In) for scintigraphic studies, or for nuclear magnetic resonance (nmr) imaging (also known as magnetic resonance imaging, mri), a label such as gadolinium, manganese or iron, or a positron-emitting isotope such as iodine-124, fluorine-19, carbon-13, nitrogen-15 or oxygen 17.

The compounds of the invention may be prepared in a sterile, nonpyrogenic medium and injected into the bloodstream of a patient at a dose to be determined in the usual way by the physician or radiologist. After a sufficient period for a good balance to have been reached between (i) specificity of binding to activated endothelium compared to non-specific distribution and (ii) total amount of compound on activated endothelium, the compound is imaged in a conventional way, according to the nature of the label used.

The compounds of the invention could also be used as laboratory probes to test for the presence of a selectin receptor such as a receptor of ELAM-1 in a sample. Such probes are preferably labeled such as with a radioactive label. There are a number of known labels including radioactive labeled atoms, e.g. radioactive C, O, N, P, or S, fluorescent dyes and enzyme labels which can be attached to compounds of the invention using known procedures. Labels as well as methods of attaching labels to sugar moieties are disclosed in U.S. Pat. No. 4,849,513 issued Jul. 18, 1989 to Smith et al. which patent is incorporated herein by reference to disclose labels and methods of attaching labels.

EXAMPLES

The following examples are provided so as to provide those of ordinary skill in the art with a complete disclosure and description of how to make compounds and compositions of the invention and are not intended to limit the scope of what the inventors regard as their invention. Efforts have been made to insure accuracy with respect to numbers used (e.g., amounts, temperature, etc.) but some experimental errors and deviation should be accounted for. Unless indicated otherwise, parts are parts by weight, temperature is in degrees C, and pressure is at or near atmospheric.

It is important to note that the invention compounds described below have 4 to 12 atoms associated with the lactose core of the tetrasaccharides that separate sialic acid from fucose, or that separate analogues or derivatives of sialic acid from fucose and vice versa.

Example 1

1-O-(2,3,4-tri-O-benzyl-α-L-fucopyranosyl)-Hexane-6-ol (3)

Hexane-1,6-diol (6 g. 25 mole was dissolved in 2:1 1,2 dichloroethane-N, N-dimethyformanide (30 mL), Bu$_4$NBr (4.0 g,) was added and the mixture was stirred at R.T. (3 h) under inert (argon) atmosphere. A solution of methyl 2,3,4-tri-O-benzyl-1-L-fucopyranosyl bromide [prepared by the reaction of 2,3,4-tri-O-benzyl-thio-α-L-fucopyranoside (1 g) with bromine (70 μl)] in dichloroethane (1 mL) was added into the reaction mixture. T.L.C. (5:1:0.5 Toluene-Acetone-MeOH) showed formation of product. Multiple elution on T.L.C. (6:1×1 and 8:1×2 Toluene-Ethyl acetate) indicated one major (RF=0.34) and one minor (Rf=0.30) product. Filtration, evaporation and column chromatographic purification afforded the title compound 3 (major product) as a syrup (730 mg), $[\alpha]^{22}_D$–44°, $[\alpha]^{22}_{436}$–79°(c, 2.2 CHCl$_3$). $^1$H-NMR (CDCl$_3$): 7.5–7.2 (m, 15H, aromatic), 5.00–4.61 (m, 7H, 3 CH$_2$ Ph, H-Fucp), 4.78 (d, J 3.4 Hz, H-1 fuc1), 4.03 (dd, 1H, J 3.5 Hz, 10.1 Hz, H-2 Fucp), 3.93 (dd, 1H, J 2.75 Hz; 10.2 Hz, H-3 Fucp), 3.86 (bq, 1H, J 6 Hz, H-5 Fucp), 3.64 (bd, 1H, J 2.1 Hz, H-4 Fucp) 3.58 and 3.42 (2 m, 2H —CH$_2$) and 1.1 (d, 3H, J 6.51 Hz, CH$_2$OH), 3.54 (t, 2H, J 6.6 Hz, —OCH$_2$—), 2.0 (bs, 1H, —OH), 1.62 and 1.52 (2 m, 4H 2CH$_2$), 1.35 (m, 2CH$_2$) and 1.1 (d, 3H, J 6.51 Hz, CH$_3$ Fucp). $^{13}$C-NMR (CDCl$_3$): δ 138.9, 138.5 (3 C-1 Ph), 97.3 (C-1), 79.3, 77.7, 76,43 (C-2), 66.07 (C-5), 7–4.7, 73.18, 73.15 (3 CH2 Ph), 67.99, 62.56 (2 OCH$_2$) 32.5, 29.3, 25.97, 25.48 (4CH$_2$) and 16.6 (CH$_3$). Calcd. for C$_{33}$HA$_2$O$_6$, Exact Mass: 534.29. Found by f.a.b.-m.s.: 535.6 (M+1)$^+$, 580.0 (M+NO$_2$)$^-$, 687.8 (M+NBA)$^-$.

Further elution afforded the mixture of α, and β fucosides (65 mg) followed by the pure β-anomer, (140 mg), $[\alpha]^{22}_D$– 0.85, $[\alpha]^{22}{436}$–1.8 (c 1.77, CHCl$_3$); $^1$H-NMR (CDCL$_3$): δ 4.3 (d, 1H, J 7.7 Hz, H-1), 3.8 (dd, 1H, J 7.7 Hz); 1.17 (d, 3H, J 6.4 Hz, CH$_3$) $^{13}$NMR (CDCL$_3$); δ 103.8(C-1), 82.5, 79.4 (C-3), 76.2 (C-2), 70.2 (C-5, moved downfield), 75.1 (C-4, moved downfield), 74.5, 73.1, 69.6, 62.8, 32,6, 29.7, 25.9, 25.5 (6 CH$_3$), 16.86 (CH$_3$). Total yield 935 mg (81%).

Example 2

Methyl 5-Acetamido-4.7.8,9-tetra-O-acetyl-3,5-di-deoxy-2-O-[6-O-(2,3,4-tri-O-benzyl-α-L-fucopyranosyl) Hexyl-D-glycero-α-D-galacto-2-nonulopyranosonate(5)

Compound 3 (329 mg) and 4(970 mg) were dissolved in dry propionitrile (5.0 mL), molecular sieve 4A° (1 g) was added and the mixture was stirred for 2 h at R.T. Silver Triflate (1.1 g) was added and the septum sealed flask, containing the mixture was cooled to −73° C. A solution of methyl sulfenyl bromide (950 μl) in dichloroethane (989.9 mg/2.55 mL was injected into the reaction mixture.

After 2 h, the reaction was terminated by the addition of a solution of Et$_3$N in CHCl$_3$ (1 mL in 5 mL), filtration, washing with water, drying (MgSO$_4$), filtration and evaporation of the organic layer afforded crude product mixture which was column chromatographically purified to afford the name compound 5 (178 mg, 30%) as a syrup $[\alpha]_D$–24°; $[\alpha]_{436}$–42.3° (c 1.55, CHCl$_3$). $^1$H-NMR (CDCl$_3$). δ 7.4–72.5 (m, arom), 5.38 (m, H-8 Neu5Ac), 5.35–531 (2d, H-7 Neu5AC), 5.20 (d, NH), 5.00–4.63 (bd, 3 CH$_2$Ph), 4.77 (d, J 3.8 Hz, H-1 Fuc), 4.31 (2dd, H-9a Neu5Ac), 4.02 (2dd, H-2 Fuc), 2.75 (dd, J 467 Hz, 12.82 Hz, H-3e Neu5Ac), 1.56 [bm, 4H, (CH$_2$)$_2$], 1.31 [bm, 4H, (CH$_2$)$_2$], 1.10 (d, J 6.53 Hz, CH$_3$ Fuc). $^{13}$C-NMR (CDCl$_3$): δ 170.019, 170.648, 170.257, 170.151, 170.060, 168.498 (6CO), 138–998, 138–725, 138–604 (3 Cl-Ph), 98.72 (C2, Neu5Ac), 97.38 (C-1 Fuc), 74.77, 73.25, 73.16, 67.98, ,65.01, 62.34, (3-OCH$_2$Ph, 2-OCH$_2$—CH$_2$, C-9 Neu5Ac), 52.63 (OCH$_3$), 49.34 (C-5 Neu5Ac), 38.09 (C-3 Neu5Ac), 29.55, 29.36, 25.90, 25.71 (4CH$_2$—), 23.18 (NCOCH$_3$), 21.2, 20.86, 20.79 (1:2:1, OCOCH$_3$) and 16.65 (CH$_3$ Fuc).

Example 3

1-O-α-Neu5Ac-(6-O-α-L-Fucopyranosyl)-Hexane (6, GM 1398)

Compound 5 was deacetylated in methanol using sodium methoxide. After neutralization with cationic resin (IR120-H[30]) at ~0°–5° C., the solution was filtered and evaporated to give a syrup. The syrupy material was dissolved in 1:1 10% aqueous methonol-p-dioxane (5 mL) and reacted with 0.2M aqueous potassium hydroxide (1.5 mL) for 15 h at 0° C.—r.t. The reaction mixture was neutralized with IR 120 (H+), filtered and evaporated to give a syrup ($R_f$=0.37, TLC in 2:1 $CHCl_3$-10% aq. MeOH). This material was dissolved in 10% aq. MeOH (5 ml) and hydrogenated at atmospheric pressure over 5% Pd-C (100 mg). TLC of the hydrogenated product showed only one product ($R_f$=0.06, 2:1 $CHCl_3$-10% aq. MeOH). The reaction mixture was filtered through Celite, concentrated, and the product was purified by chromatography from a biogel P2 column using water as the eluant. Appropriate fractions were pooled and lyophilized to afford pure 9. $^1$H-NMR data ($D_2O$-acetone): δ 4.85 (d, J 3.85 Hz, 1H-fuc), 402 (q, 1H, H-5 fuc), 3.85–3.35 (ring protons and 2$OCH_2$), 2.7 (dd, J 4.64 Hz, H-3e Neu5Ac), 2.0(s, 3H, $NHCOCH_3$), 1.65–1,45 (m, 5H, H-3a Neu5Ac and 2 $CH_2$), 1.35 (bm, 4H, 2$CH_2$) and 1.18 (d, J 6.65 Hz, $CH_3$-Fuc). Molec. Formula, $C_{23}H_{41}NO_{14}$ (Mol. Wt., 555.58, Exact mass, 555.253). Found: 556.5 $(M+1)^+$, 688.2 $(M+Cs)^+$, 292.2 (2,3-dehydro Neu5Ac), 265.3 $(M-Neu5Ac)^+$ and 554.2$(M-1)^-$, 290.4 $(Neu5Ac)^-$.

Example 4

6-0-[R,S]-1-Methoxycarbonyl-ethyl]-Hexanyl-2, 3, 4-Tri-0-benzyl-α-L-Fucopyranoside (8)

Compound 1 (2.9 g, 6.2 mmoL) and 2 (37 g, 313.0 mmoL) were transferred into 500 mL flask, dried under high vacuum (8 h), and dissolved in 6:1 dichloromethane-N,N-dimethylformanide(350 mL). Molecular sieves 4A (5 g) was added and the solution was stirred (2 h), then cooled (0° C.) before the addition of $CuBr_2$ (2.33 g) and $Bu_4NBr$ (3.7 g), into it. The dark reaction mixture was stirred at R.T. (3–4 h), filtered through Celite and the total filtrate was washed with saturated $NaHCO_3$, saturated NaCl and water. The organic layer was dried ($MgSO_4$), filtered and evaporated to give a syrup. Column chromatography from dry silica gel column (400 g), using 10:1 (300 mL), 40:1 (1.5L) and 20:1 toluene-acetone afforded the pure product (7) as a syrup (1 g.). Molecular formula $C_{33}H_{42}O_6$ (Mol. wt. 534.70). Found: 535.6 $(M+1)^+$, 417.4 $(M-117)^+$ and 580.0 $(M+NO_2)$, 687.8 (M+NBA). $^1$H-and $^{13}$C-NMR indicated it to be a mixture of α- and β-L-fucopyranosides.

Compound 7 (0.97 g) was dispersed in toluene (50 mL) in a 100 mL flask equipped with Dean-Stark assembly. Toluene (15 mL) was distilled off followed by the addition of $(Bu_3Sn)_2O$ (1.52 mL) into the reaction mixture. More toluene (20 mL) was distilled off and the resulting solution was refluxed (2–3 h). All the toluene was evaporated off on a rotatory evaporator using a short neck distillation assembly fitted with a stop cock. The evacuated flask containing the stannylated material was shut off using the stop cock and removed from the rotatory evaporator. Argon was introduced into the flask followed by methyl 2-chloropropionate (1.5 mL). The content was stirred and heated (95°–100° C.) under an argon atmosphere for 12 h. The mixture was cooled, crushed ice followed by dichloromethane (15 mL) was introduced into the flask. The total content was transferred into a separatory funnel, the organic layer was washed with water, separated and dried ($MgSO_4$). Filtration and evaporation of the dichloromethane afforded crude product which was transferred on dry packed silica gel (150 g) column and eluted with toluene (120 mL) followed by 60:1 (200 mL) and 80:1 toluene-acetone. The anomeric mixture of products (8) was isolated as a syrup. $^{13}$C-NMR ($CDCl_3$-TMS):δ 170.14 (CO), 103.79 (C1 β-L-Fucp, 97.45 (C1 α-L-Fucp; α:β5.5:1), 52.8, 52.56 ($OCH_3$), 21.49 (Lactyl $CH_3$), 16.6, 16.8 ($CH_3$ of α- and β-L-Fucp).

Example 5

1-O-(α-,β-L-Fucopyranosyl)-6-O-[(R,S)-1-Carboxyethyl]-Hexane (9)

Syrupy 8 was dissolved in 10% aqueous methanol and hydrogenated (2 days) in the presence of 10% Pd-C under atmospheric pressure. Completion of the reaction was determined by TLC (5:1:0.2 toluene-acetone-10% aq. MeOH). The reaction mixture was filtered through Celite and the clear filtrate was evaporated to dryness. $^1$H-NMR of the product indicated complete absence of the aromatic signals.

The crude product was dissolved in 1:1 p-dioxane-MeOH (2.5 mL), 10% aq. MeOH (3.0 mL) was added followed by the addition of 0.2M aq. KOH (1.5 mL) at 0°–5° C. Reaction was then continued for 8–10 h at R.T. TLC (every hour in 5:1:1 toluene-acetone-10% aq. MeOH) indicated conversion into product with lower $R_f$. The reaction mixture was neutralized with IR 120 ($H_+$), filtered and evaporated. The syrup was charged on dry packed silica gel column and eluted with 5:1:1 toluene-acetone-10% aq. MeOH. The GC-MS of the pure product ($R_f$=0.17), as its permethylated derivative showed one major and one minor component (due to the α- and β-L-Fucopyranose), having the same fragmentation pattern with major m/e at 189 (2,3,4-Tri-O-methyl-L-Fucose)+, 157 [m/e 189-32($OCH_3$)], 115 and 88 [i.e. total 203 due to {O-Hexyl-O—CH(COO$CH_3$)($CH_3$)}](FIG. 3).

Example 6

Synthesis of O-Hexamethylene linked α-, β-NeuNAc and α-, β-L-Fucopyranose (GM 1222 and GM 1279)

Compound 7 (203.6 mg) and donor 4 (597 mg) were dissolved in acetonitrile (7.0 mL) and stirred (1 h) in the presence of molecular sievs 4A (2 g). Silver triflate (764 mg) was added and the mixture was cooled (−30° C.), before the addition of a solution of methyl sulfenyl bromide (355 uL of a stock solution containing 989.9 mg/2.55 mL). At the end of the reaction (2–3 h), the reaction was worked up in the usual manner and the crude product was charged on a silica gel (350 g) column and eluted successively with 5:1:0.1 (180 mL) and 7:1:0.1 (Toluene-Acetone-MeOH). The product was isolated as mixtures in two major fractions (76–83) and (84–110) respectively. $^{13}$C-NMR of both fractions showed: δ 171.0, 170.65, 170.25, 170.18, 170.15, 170.056 and 168.5 (CO), 138.99–138.57 (6 C-1 Ph), 103.79 (β-fuc C-1), 98.71 (C-2 Neu4Ac), 97.38 (α-fuc C-1), 52.63 ($OCH_3$), 49.36 (C-5 Neu5Ac), 38-08 (C-3 Neu5Ac), 29.7–29.3 (3$CH_2$), 25.9–25.7 (3$CH_2$), 23.2 ($NHCOCH_3$), 21.1–20.8 ($OCOCH_3$) and 16.88, 16.67 ($CH_3$ of α-, β-L-Fuc).

NMR indicated that the first product mixture contained larger proportions of α-fuc and β-NeuNAc.

Deprotection

Each pool of fractions were deprotected separately. Deacetylation was carried out in methanol (dry) using catalytic sodium methoxide. After neutralization (IR 120H$^+$), filtration and evaporation, the syrups were dissolved in 2:1 MeOH-P-Dioxane (3 mL) and 'saponified by the addition of 0.2M aqueous KOH (1.5 mL) to give products (R$_f$=0.35 and 0.33), T.L.C. solvent (2:1 CHCl$_3$-10% aqueous MeOH).

Expected molecular formula: C$_{44}$H$_{59}$NO (M. wt: 825.96; Exact Mass: 825.39). Found: 848.5 (M+Na)$^+$ and 824.6 (M-1).

The syrupy products were dissolved in 10% aqueous MeOH and hydrogenated over 10% Pd-C at 1 atmosphere until TLC (2:1 CHCl$_3$-10% aqueous MeOH) indicated absence of the starting compounds and appearance of new products (R$_f$=0.17). Filtration, evaporation and lyophilizations afforded two mixtures (GM 1222 and GM 1279). Expected molecular formula: C$_{23}$H$_{41}$NO$_{14}$ (M. wt. 555.552, Exact mass: 555.253). Found: 556.5 (M+1)$^+$, 578.5 (M+Na)$^+$, 292.2 (2,3-enesialic acid+1)$^+$, 265.3 (M-291)$^+$ and 554.2 (M-1).

Analysis and Testing

Figure 4:
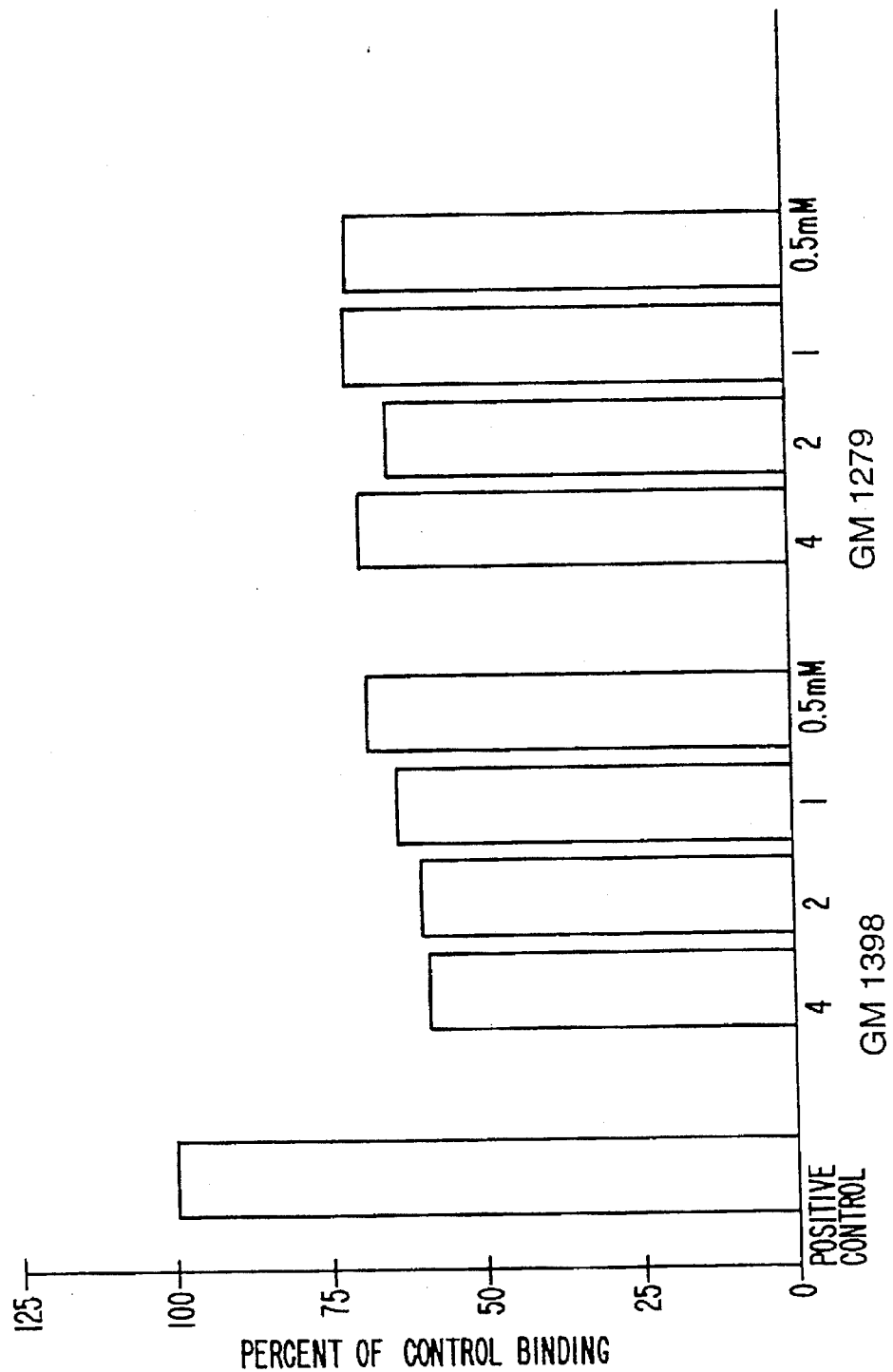
FIG. 4 is a graph showing the results of Elisa assays carried out to determine the ability of two different compounds to block the binding of 2,3,sialyl-Le$^x$ to E-selectin IgG chimera. The compounds tested were GM 1279 and GM 1398. The compounds were tested at several concentrations as shown in the figure, and the results expressed as the per cent of control binding.

Analysis and testing of two specific products referred to as GM 1279 and GM 1222 is described below. The structure of each of these compounds was shown above. Comparison of the T.L.C. of α-Neuraminidase treated GM 1222 and GM 1279 showed that both contained G-linked sialic acid as the major component. However, NMR had indicated that the first of the two mixtures contained larger proportion of α-L-fucose. These samples were individually analyzed by Dionex (Carbopak DA-1 column with isocratic running 0.1M NaOH) and were found to contain equal proportions of Fucose and Neu5Ac. The elution profile indicated the presence of four distinct signals for both GM 1222 and GM 1279, (FIG. 4). Based on the NMR information and T.L.C. data after neuraminidase treatment, the major signals, eluting at a slower rate, were designated to compounds having α-linked sialic acid. The faster eluted minor components contained β linked L-fucoside. Pool 2 (GM 1279) contained higher proportions of β-L-fucopyranoside (O-linked through hexamethylene to a O-α-sialic acid).

Example 7

Selectin Binding

An ELISA assay was employed that uses recombinant fusion proteins composed of extracellular portions of the human selectins joined to human immunoglobulin heavy chain CH3, CH2, and hinge regions. See, for example, Walz et al., Science (1990) 250:1132; Aruffo et al., Cell (1991) 67:35; Aruffo et al., Proc. Natl. Acad. Sci. USA (1992) 89:2292. The assay is well known in the art, and generally consists of the following three steps:

I. 2,3sLex glycolipid (25 picomole/well) was transferred into microtiter wells as solutions and then evaporated off. Excess, which remained unattached, was washed off with water. The wells were then blocked with 5% BSA at room temperature for an hour and then washed with PBS containing 1 mM calcium.

II. Preparation of "multivalent" receptor of the Selectin-IgG chimera was carried out by combining the respective chimera 1 μg/mL) with biotin labelled goat F(ab')$_2$ anti-human IgG (Fc specific) and streptavidin-alkaline phosphatase diluted 1:1000 in 1% BSA-PBS (1 mM calcium) and incubating at 37° C. for 15 min. This allowed. the soluble multivalent receptor complex to form.

III. Potential inhibitors such as compound of formula I(a) were allowed to react with the soluble receptor at 37° C. for 45 min. This test assumes that optimal binding, between the soluble phase receptor complex and the inhibitor (non natural ligand), would have occurred within this time frame. This solution was then placed in the microtiter wells that were prepared in step I. The plate was incubated at 37° C. for 45 minutes to allow the soluble receptor to bind to its natural ligand. In the presence of a strong inhibitor only a few receptors should be free to bind to the microtiter plate coated with the natural ligand.

The positive control is the signal produced by the soluble receptor when it is allowed to react with 2,3sLex glycolipid in the microtiter wells in the absence of any inhibitor. This was considered 100% binding. The signal produced by the receptor that had been previously treated with an inhibitor (recorded as O.D.), was divided by the signal produced by the positive control and multiplied by 100 to calculate the % receptor bound to the well, or as expressed in the figures, the per cent of control binding. Several of the compounds described herein were tested using this assay.

Figure 5:
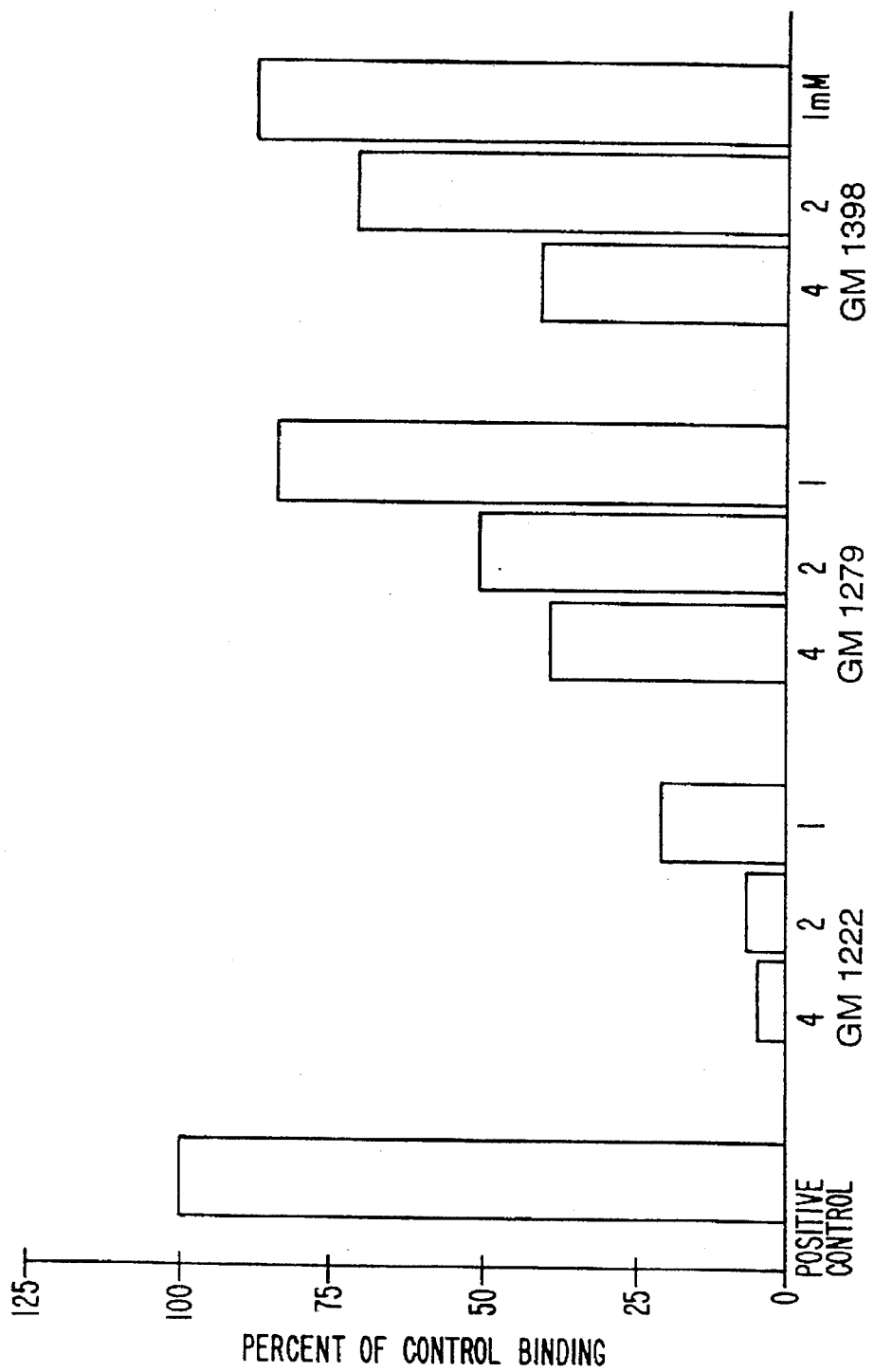
FIG. 5 is a graph showing the results of Elisa assays carried out to determine the ability of three different compounds to block the binding of 2,3,sialyl-Le$^x$ to L-selectin IgG chimera. The compounds tested were GM 1222, GM 1279 and GM 1398. The compounds were tested at several concentrations as shown in the figure. The results are expressed as per cent of control binding.

The results shown in FIG. 4 show that both GM 1279, and GM 1398 inhibit E-selectin binding to 2,3sLex glycolipid. FIG. 5 shows that GM 1279, and GM 1398 also inhibit L-selectin binding in a concentration dependent manner. Further, the figure also shows that GM 1222 blocks L-selectin binding at concentrations lower than GM 1279 and GM 1398.

The structures of GM 1398: GM 1279, and GM 1222, are shown below.

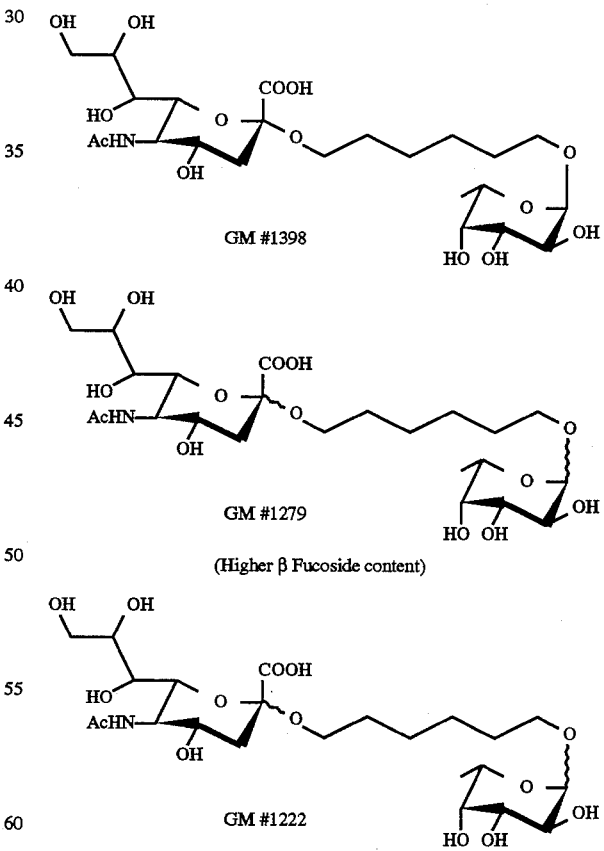

Figure 6:
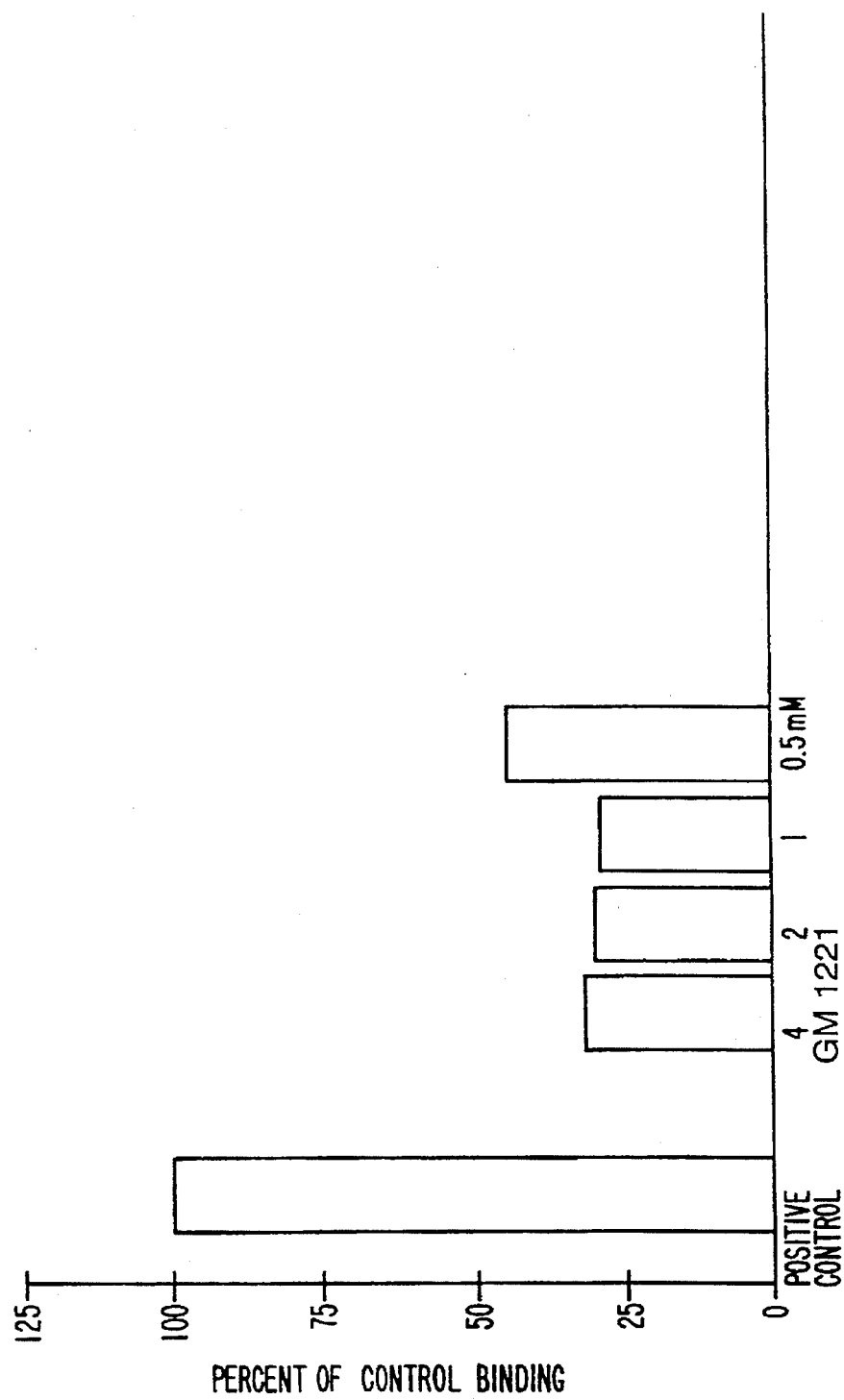
FIG. 6 is a graph showing the results of Elisa assays carried out to determine the ability of GM 1221 to block the binding of 2,3,sialyl-Le$^x$ to L-selectin IgG chimera. The results are expressed as per cent of control binding.

The results shown in FIG. 6 indicate that the compound GM 1221 inhibits L-selectin binding to 2,3sLex glycolipid. Note that at all four concentrations of the compound tested there is significant inhibitory activity. The structure of GM 1221 is shown below:

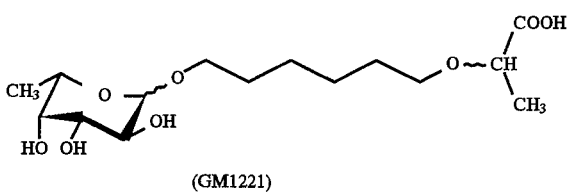

(GM1221)

In addition to the ligands described above, other ligands could be obtained by selecting more rigid spacers in order to maintain the appropriate statistical average distance between the sialic acid and fucose moieties in space thereby improving the inhibitory property of such structures towards the selectins. Further modifications of these compounds e.g., attaching them through chemical linkages on appropriate molecular supports and use of analogs or derivatives of sialic acid and L-fucose are also considered to be within the scope of the present invention.

Example 8

Treatment of Sepsis

A number of the complications associated with sepsis arise from unwanted neutrophil extravasation and adhesion of the neutrophils to the endothelium. The invention compounds GM 1221, GM 1222, GM 1398 and GM 1279 would be used to prevent or treat sepsis.

The effectiveness of these compounds would be shown in a baboon sepsis model system as described by Taylor et al., *J. of Clinical Inv.*, (1987), 79:918, and by Taylor, et al., *Circulatory Shock*, (1988), 26:227. Briefly, this would consists of determining if the compounds are effective in treating sepsis by preventing the death, or prolonging the lives of septic animals to either a lethal or sublethal dose of *E. coli*. A lethal or sublethal dose of *E. coli* consist of approximately $4 \times 10^{10}$ and $0.4 \times 10^{10}$ organisms, respectively. Baboons that receive a lethal dose of *E. coli* invariably die within 16–32 hours. Taylor, et al., *J. of Clinical Inv.*, (1987), 79:918, and Taylor, et al., *Circulatory Shock*, (1988), 26:227.

Thus, the procedure would consist of using two administration routines for each of the three compounds wherein they are delivered in physiological saline. In the first, between 1 and 10 mg of compound per kg of body weight is administered in three separate doses at 24, 22, and 21 hours before a lethal challenge of bacteria. Alternatively, compound can be administered in a single dose simultaneously with the bacterial challenge. In both instances the compounds would considerably extend the lifetime of the baboons that receive the multiple or single dose treatment and they would survive well beyond 48 hours.

Example 9

Treatment of Peritonitis

Certain of the invention compounds have been shown to be efficacious in treating peritonitis. The efficaciousness of GM 1221, and GM 1398 was shown using a murine thioglycollate induced peritonitis model. The assay. materials and methods are known in the art, or are generally described by Lewinsohn, D. et al., *J. Immun.*, 138:4313–4321 (1987), or Watson, S. et.al., *Nature* 349:164–166 (1991).

This assay measures the ability of the compounds to inhibit neutrophil migation to the peritoneal cavity, the migration being initiated by the presence of thioglycollate in the peritoneal cavity. Thioglycollate is a known and effective inflammatory agent that causes neutrophil migration into the mouse peritoneum when it is administered intraperitoneally. Lewinsohn, D. et al., *J. Immun.* (1987) 138:4313–4321.

Briefly, female Swiss Webster mice weighing about 25 grams were injected in the tail vein with 200 ul of phosphate buffered saline (PBS) with or without the appropriate compound. The pH of the solutions was adjusted to neutrality by the addition of either NaOH or HCL and sterilized by filtration through a 0.2 u filter.

Immediately following injection with the appropriate compound or PBS, the mice were injected intraperitoneally with 1 ml of thioglycollate medium prepared as described by the manufacturer, BBL. Three hours following injection of the thioglycollate solution the mice were sacrificed by $CO_2$ asphyxiation, and the number of cells in the peritoneum removed by lavage with 5 ml of heparinized (5 U/ml) 0.9% sodium chloride solution containing 0.1% bovine serum albumin. Cell number was determined using a Coulter Counter. The cells were prepared for counting by diluting the lavage fluid with 1:50 of a commercial physiological isotonic solution, Isoton II, and the cells-lysed by adding S/P Lysing and Hemoglobin Reagent (1:100 final dilution). Cell nuclei were counted in a sized window with lower and upper limits set at 3.9 and 5.7 um, respectively.

FIG. 7 shows the results. It is apparent that both GM 1398 and GM 1221 inhibit neutrophil migration into the peritoneum. However, the better compound is GM 1398 which inhibited about 30% more neutrophils migration than GM 1221.

The instant invention is shown and described herein in what is considered to be the most practical and preferred embodiments. Publications listed herein are incorporated herein by reference to disclose specific procedures on how to make, and/or use the invention. Further, it is recognized that departures may be made therefrom which are within the scope of the invention, and that obvious modifications will occur to one skilled in the art upon reading this disclosure.

What is claimed:

1. An assay reagent for determining the presence of a selectin receptor in a sample comprising:

a substrate having a surface wherein a compound is bound to the surface and the compound comprises the formula:

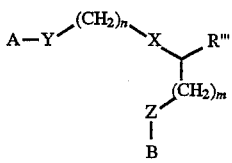

wherein m and n are independently an integer of from 1 to 5, Y and Z are independently a connecting moiety selected from the group consisting of —$CH_2$—, —O—, —S—, —NR'— and —NR'R" (wherein R' and R" are independently H or an alkyl containing 1 to 5 carbon atoms); X is a connecting moiety which is selected from the group consisting of —O—, —S—, —NR'—, and a covalent bond; and wherein R'" is selected from the group consisting of 1) hydrogen;
2) an alkyl containing 1 to 4 carbon atoms;

3)

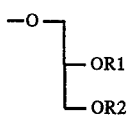

wherein R¹ and R² are independently an alkyl or an alkenyl group of 1–5 or 13–15 carbon atoms;

4)

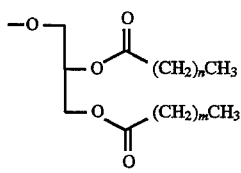

wherein $(CH_2)_n{'}$ and $(CH_2)_m{'}$ are independently a saturated or unsaturated alkyl group of 15 to 24 carbon atoms;

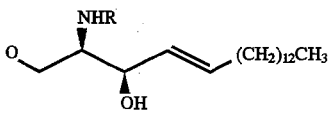

5) wherein R is —$CO(CH_2)_{14}CH_3$;

6)

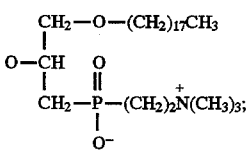

7)

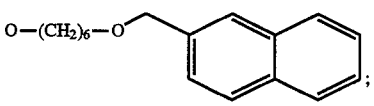

8)

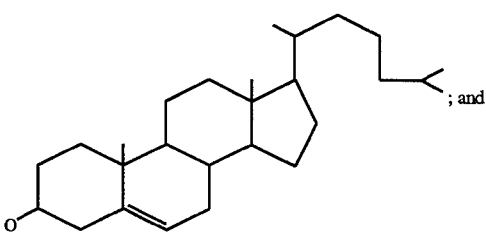

9) —OR", SR", —I, —$N_3$, and NR'R";

wherein A is selected from the group consisting of α and β forms of sialic acid, Kemp's acid, Quinic acid, Glyceric acid, Lactic acid, acetic acid, —$SO_3$, —$PO_3$, and esters thereof; and wherein B is selected from the group consisting of α and β forms of L-fucose, carboxylic acid analogues of fucose, inositol, substituted inositol, benzimidazole, substituted benzimidazole, guanidine, substituted butane, pentaerythritol, and substituted pentaerythritol, wherein the substituents are selected from the group consisting of —$CH_3$, —$CH_2OH$, —$CH_2F$, and —$CH_2NR^3{_2}$ wherein each $R^3$ is independently an alkyl of 1 to 5 carbon atoms; and

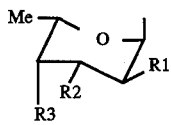

wherein Me is a methyl group, R1, R2, and R3 are each independently —OH, —F, and —NR"R" wherein each R" is independently hydrogen or an alkyl of 1 to 5 carbon atoms.

2. An assay reagent as in claim 1, wherein A is

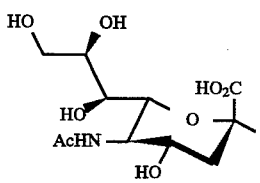

and B is

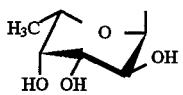

and esters thereof.

3. An assay reagent as in claim 1, wherein A is selected from the group consisting of glyceric acid, lactic acid, acetic acid, —$SO_3$ and —$PO_3$.

4. An assay reagent as in claim 1, wherein the compound is:

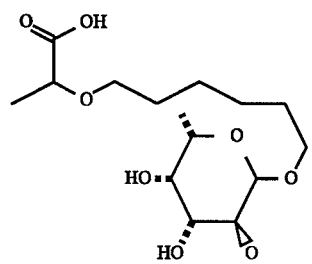

5. An assay reagent as in claim 1, wherein the compound is:

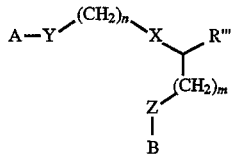

wherein m and n are independently an integer of from 1 to 5, Y and Z are independently a connecting moiety selected from the group consisting of —CH₂—, —O—, —S—, —NR'—and —NR'R"— (wherein R' and R" are independently H or an alkyl containing 1 to 5 carbon atoms); X is a connecting moiety which is selected from the group consisting of —O—, —S—, —NR'—, and a covalent bond; and wherein R'" is selected from the group consisting of
1) hydrogen;
2) an alkyl containing 1 to 4 carbon atoms;
3)

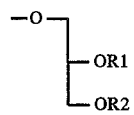

wherein R¹ and R² are independently an alkyl or an alkenyl group of 1–5 or 13–15 carbon atoms;
4)

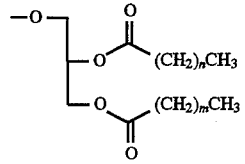

wherein (CH₂)ₙ' and (CH₂)ₘ' are independently a saturated or unsaturated alkyl group of 15 to 24 carbon atoms;
5)

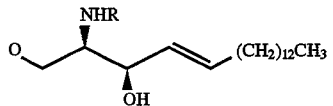

wherein R is —CO(CH₂)₁₄CH₃;
6)

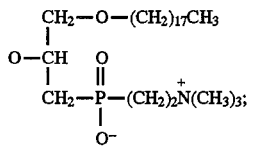

7)

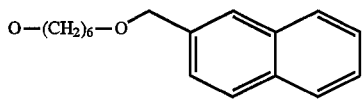

6. An assay reagent as in claim 1, wherein the compound is:

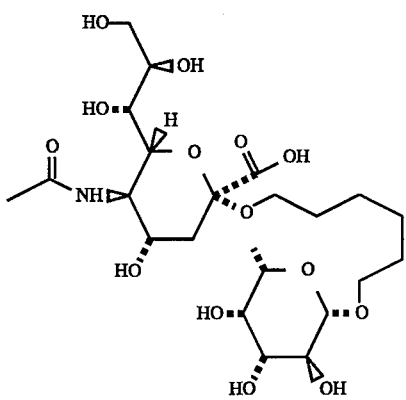

7. An assay reagent as in claim 1, wherein the compound is:

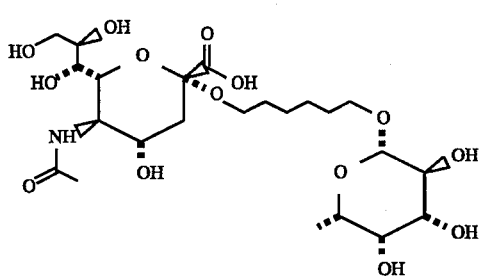

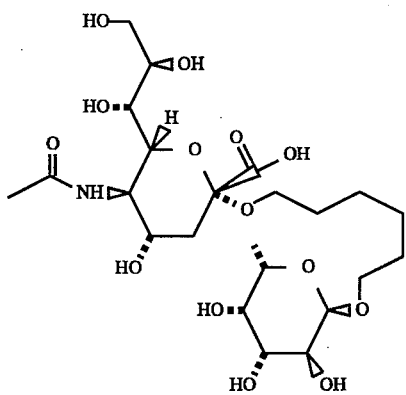

8. An assay reagent as in claim 1, wherein the compound is an ELAM-1 receptor.

9. An assay reagent as in claim 1 wherein:
m is 2;
n is 2;
Y is —O—;
Z is —O—;
X is —CH₂—;
R'" is hydrogen; and
B is selected from the group consisting of α-L-fucose and β-L-fucose.

10. An assay reagent as in claim 9, wherein A is N-acetyl neuraminic acid.

11. A method of assaying for the presence of a selectin receptor in a sample, comprising the steps of:
attaching a compound to a surface of a support, wherein the compound comprises the formula:

8)

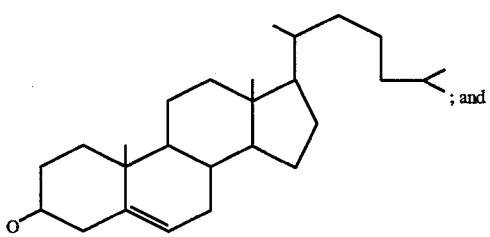
; and

9) —OR", SR", —I, —N₃, and NR'R";

wherein A is selected from the group consisting of α and β forms of sialic acid, Kemp's acid, Quinic acid, Glyceric acid, Lactic acid, acetic acid, —SO₃, —PO₃, and esters thereof; and wherein B is selected from the group consisting of α and β forms of L-fucose, carboxylic acid analogues of fucose, inositol, substituted inositol, benzimidazole, substituted benzimidazole, guanidine, substituted butane, pentaerythritol and substituted pentaerythritol, wherein the substituents are selected from the group consisting of —CH₃, —CH₂OH, —CH₂F, and —CH₂NR³₂, wherein each R³ is independently an alkyl of 1 to 5 carbon atoms; and

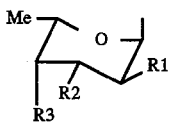

wherein Me is a methyl group, R1, R2, and R3 are each independently —OH, —F, and —NR"R" wherein each R" is independently hydrogen or an alkyl of 1 to 5 carbon atoms; and contacting the sample with the surface of the substrate; and determining the presence of selectin receptors bound to the surface of the support.

12. A method as in claim 11, wherein A is:

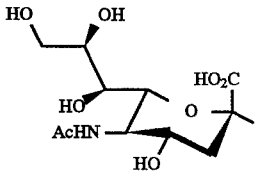

and B is:

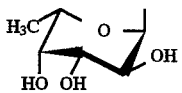

and esters thereof.

13. A method as in claim 11, wherein A is selected from the group consisting of glyceric acid, lactic acid, acetic acid, —SO₃ and —PO₃.

14. A method as in claim 11, wherein the compound is:

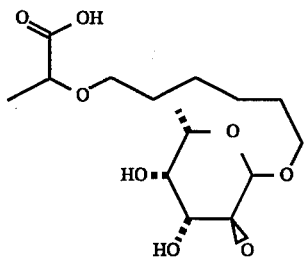

15. A method as in claim 11, wherein the compound is:

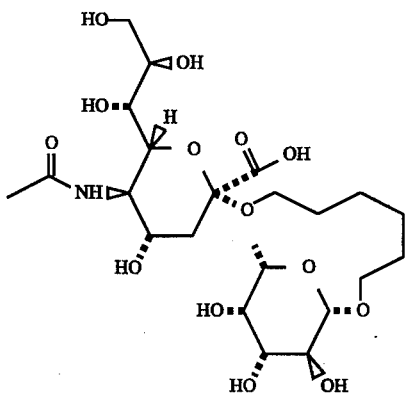

16. A method as in claim 11, wherein the compound is:

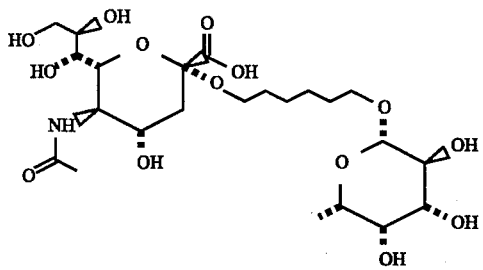

17. A method as in claim 11, wherein the compound is:
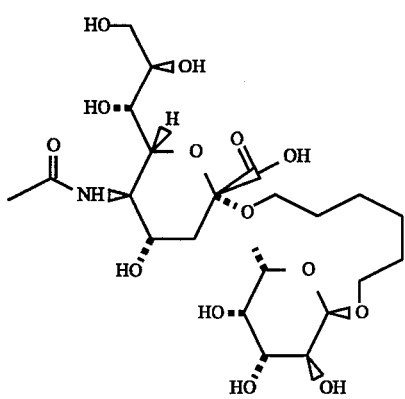
18. A method as in claim 11, wherein the selectin receptor is an ELAM-1 receptor.
19. A method as in claim 11 wherein:
m is 2;
n is 2;
Y is —O—;
Z is —O—;
X is —CH₂—;
R'" is hydrogen; and
B is selected from the group consisting of α-L-fucose and β-L-fucose.
20. A method as in claim 19 wherein A is N-acetyl neuraminic acid.
* * * * *